US008670825B2

(12) United States Patent  
Min et al.

(10) Patent No.: US 8,670,825 B2  
(45) Date of Patent: Mar. 11, 2014

(54) METHOD AND SYSTEM FOR DISCRIMINATION OF VT AND SVT ARRHYTHMIAS

(75) Inventors: Xiaoyi Min, Thousand Oaks, CA (US); Eliot L. Ostrow, Sunnyvale, CA (US)

(73) Assignee: Pacesetter, Inc., Sylmar, CA (US)

( * ) Notice: Subject to any disclaimer, the term of this patent is extended or adjusted under 35 U.S.C. 154(b) by 21 days.

(21) Appl. No.: 13/563,311

(22) Filed: Jul. 31, 2012

(65) Prior Publication Data

US 2014/0039332 A1  Feb. 6, 2014

(51) Int. Cl.
*A61N 1/00* (2006.01)

(52) U.S. Cl.
USPC .......................................................... 607/5

(58) Field of Classification Search
USPC ....................................... 607/4–28
See application file for complete search history.

(56) References Cited

U.S. PATENT DOCUMENTS 7,130,677 B2  10/2006  Brown et al.
7,149,577 B2  12/2006  Sharma et al.
7,983,752 B2  7/2011  Doerr et al.

*Primary Examiner* — Scott Getzow

(57) ABSTRACT

Methods and systems are provided for discriminating heart arrhythmias. The methods and systems include identifying an arrhythmia, recording a predetermined number of beats during the arrhythmia as a base arrhythmia (BA) beats; delivering anti-tachy pacing (ATP) therapy to at least one chamber of the heart. After delivering the ATP therapy, the methods and system record at least one return beat representing cardiac activity following the ATP therapy, determines whether the return beat originated in a reference chamber of the heart, compares a morphology of the return beat to a morphology of the BA beat; and declares a VT or SVT based on the comparing operation.

20 Claims, 15 Drawing Sheets

Correct Classification of Sinus Tachy by Samir and Min

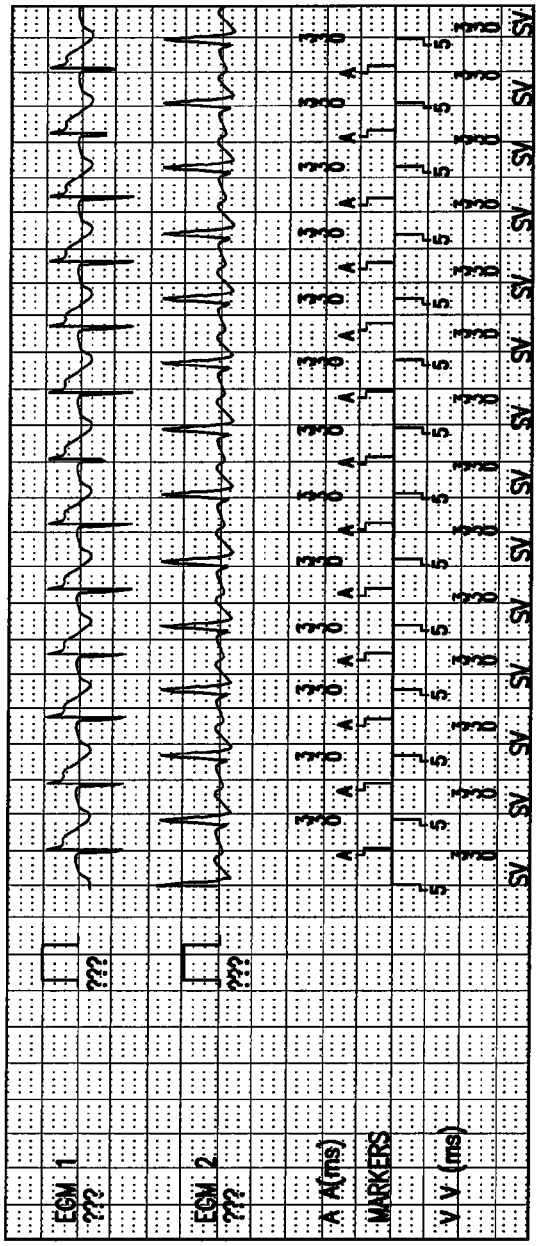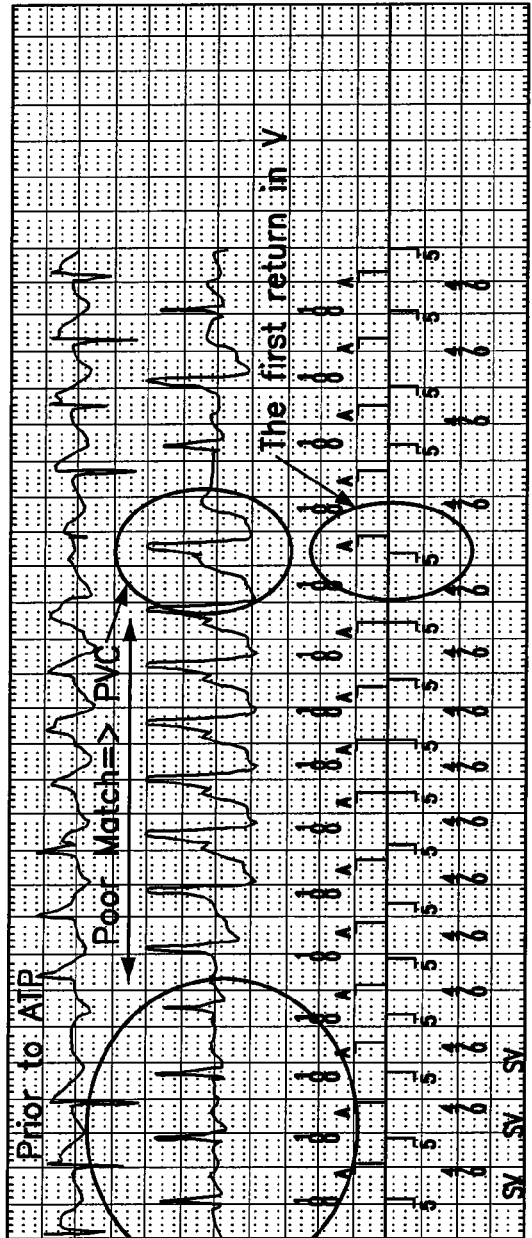
FIG. 5C  Example of misclassified ST due to PVCs by Samir's but correct by Min's Example of 1:1 VT termination

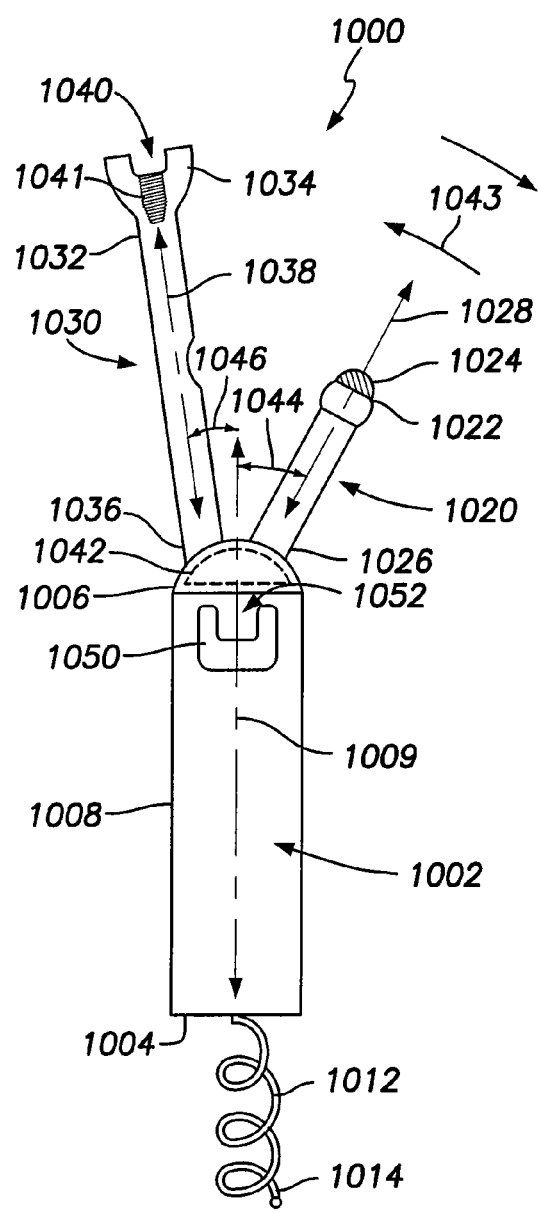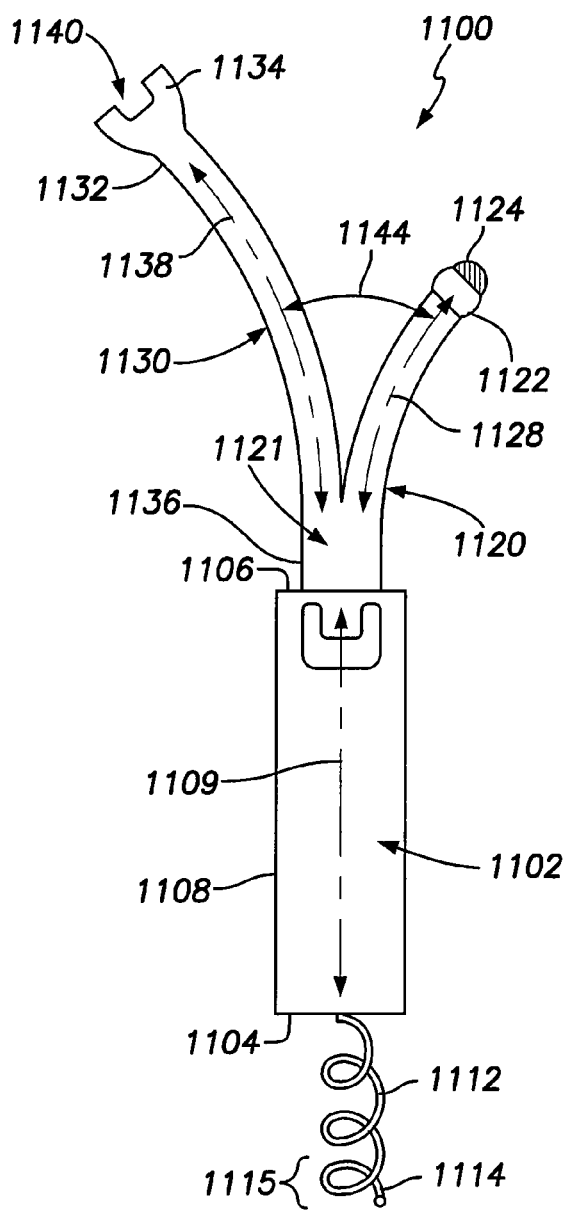
FIG. 10
FIG. 11

METHOD AND SYSTEM FOR DISCRIMINATION OF VT AND SVT ARRHYTHMIAS

FIELD OF THE INVENTION

Embodiments of the present invention generally relate to arrhythmia discrimination, and more specifically to methods and systems that discriminate between VT and SVT arrhythmias.

BACKGROUND OF THE INVENTION

Numerous types of devices and systems exist today that monitor and treat abnormal behavior of the heart (arrhythmias). Examples of arrhythmias include tachycardia, fibrillation and the like. With normal conduction, the cardiac contractions are very organized and timed so that the top chambers (the atria) contract before the lower chambers and the heart rate is maintained between 60 and 120 beats per minute. Fast, abnormal heart rhythms are called tachyarrhythmias. Ventricular tachycardia (VT) is a tachyarrhythmia that originates in the ventricle and may be life-threatening. Symptoms of VT include feeling faint, sometimes passing out, dizziness, or a pounding in the chest.

Supraventricular tachycardia (SVT) refers to a rapid heart rhythm originating above the ventricular tissue. Supraventricular tachycardias can be contrasted to ventricular tachycardias—rapid rhythms that originate within the ventricular tissue. Although an SVT can be due to any supraventricular cause, the term is often used to refer to one specific cause of SVT, namely Paroxysmal supraventricular tachycardia (PSVT) which is due to AV nodal reentrant tachycardia.

Tachycardias can result due to any number of reasons. For example, patients who have had myocardial infarctions, or other diseases that create scarring in the ventricular region of the heart, often develop monomorphic ventricular tachycardias. A monomorphic ventricular tachycardia (MVT) is a type of tachycardia that originates from one ventricular focus. These tachycardias often arise in and around an area of scarring on the heart. They are typically uniform and typically occur at a regular rate. Faster MVTs are often associated with hemodynamic compromise, whereas slower MVTs can be very stable.

SVTs and VTs may be treated with medication, catheter ablation, surgery, and an implantable medical device (IMD). The IMD may treat VT or SVT by pacing the heart, such as antitachycardia pacing (ATP) or, when ATP does not terminate the arrhythmia, delivering a high voltage shock to terminate the arrhythmia.

Numerous conventional algorithms exist to discriminate VT and SVT through passive approaches. These passive algorithms discriminate between different arrhythmias based on the morphology of one or more prior cardiac beats or events/cycles. The conventional passive algorithms also utilize one or more prior cardiac events/cycles to determine physiologic behavior such as the RR interval, AR interval, EGM width, RR regularity, onset, and morphology (bipolar and far-field) and the like.

However, conventional passive rhythm discrimination methods have experienced certain limitations. For example, conventional passive rhythm discrimination methods may be unable to differentiate between VT and SVT. Further, polymorphic VT may be irregular which in turn leads to mischaracterization by certain passive rhythm discrimination methods. Also, passive rhythm discrimination methods may be susceptible to variation in variables associated with the IMD electronics, such as conduction aberrance, signal truncation or misalignment, saturation of electrodes after shocks and the like.

Various passive rhythm discrimination implementations are used today, each of which affords different sensitivity and specificities. For example, different manufactures use different morphology methods (e.g., alignment of peaks in cardiac events, use of wavelets, and the like). The accuracy of these methods depends on multiple variables, such as signal mismatch. Signal mismatch may be caused by signal truncations, position of the starting points, and near field sensitivity. Some passive rhythm discrimination methods store templates that may also be somewhat different from the real time signals. The differences between templates and real signals may lead to mischaracterization, and different levels of sensitivity and specificity.

More recently, it has been proposed to utilize an active discrimination method which involves, upon detecting an arrhythmia, immediately delivering an anti-tachy pacing (ATP) therapy to the right atrium (RA) and the right ventricle (RV). The ATP therapy is delivered without delay as soon as an arrhythmia is detected. The active discrimination method then determines whether the arrhythmia persists. If the arrhythmia persists, then the first returned beat is considered the origin of the arrhythmia. When the arrhythmia persists, the active discrimination method next determines which chamber exhibits the first returned beat, namely the chamber in which the next cardiac cycle begin. If the first returned beat originates in the RA, the arrhythmia is declared to be a SVT. If the first returned beat originates in the RV, the arrhythmia is declared to be a VT.

However, this active discrimination method experiences certain limitations. For example, a post ventricular contract (PVC) or a post atrial contraction (PAC) may cause mischaracterization of an arrhythmia. Also, in certain instances, the heart may experience oscillations or aberrations at the end of an ATP therapy. When PVC, PAC, oscillation or aberration occurs, a risk exists that the PVC, PAC, oscillation or aberration may cause the arrhythmia to be mischaracterized as VT when the arrhythmia is in fact SVT, or mischaracterized as SVT when the arrhythmia is in fact VT.

SUMMARY

In accordance with one embodiment, a method is provided for discriminating heart arrhythmias. The method includes identifying an arrhythmia, recording a predetermined number of beats during the arrhythmia as a base arrhythmia (BA) beats; delivering anti-tachy pacing (ATP) therapy to at least one chamber of the heart. After delivering the ATP therapy, the method records at least one return beat representing cardiac activity following the ATP therapy, determines whether the return beat originated in a reference chamber of the heart, compares a morphology of the return beat to a morphology of the BA beat; and declares a VT or SVT based on the comparing operation.

The method may declare a VT when the morphology of the return beat corresponds to the morphology of the BA beat. The method further comprising determining whether the arrhythmia persists following delivery of the ATP therapy. The determining operation may include determining whether the return beat originates in a ventricle as the reference chamber. The determining operation may include determining whether the return beat originates in an RA or RV as the reference chamber. The BA morphology may be derived from a series of at least 3 beats as the predetermined number of beats. The delivering operation may include delivering the ATP therapy to both of the RV and RA. The comparing operation may include comparing a QRJ complex of the return beat and the BA beat. The return beat represents a first intrinsic cardiac event that occurs immediately after completion of the ATP therapy. The BA beat and the return beat are recorded over each of atrial and ventricular channels. The comparing operation includes comparing BA and return beats recorded over an atrial channel or a ventricular channel when the return beat originates in the RA or RV, respectively.

Optionally, the comparing operation includes at least one of the following: i) comparing shapes of the BA and return beats; ii) comparing a number of peaks in the BA and return beats; iii) comparing an area under curves defined by the BA and return beats; iv) comparing a number of polarity changes in the BA and return beats, and v) comparing a number of positive and negative peaks in the BA and return beats.

In accordance with an embodiment, a system is provided for discriminating heart arrhythmias. The system comprises inputs configured to receive cardiac signals representative of heart beats; an arrhythmia module configured to identify an arrhythmia; a processor configured to record in memory the cardiac signals for a predetermined number of beats, during the arrhythmia, as a base arrhythmia (BA) beats; and a therapy module configured to deliver anti-tachy pacing (ATP) therapy to at least one chamber of the heart. The processor is configured to record in the memory, after delivering the ATP therapy, the cardiac signals for at least one return beat representing cardiac activity following the ATP therapy. An origin module is configured to determine whether the return beat originated in a reference chamber of the heart. A morphology module is configured to compare a morphology of the return beat to a morphology of the BA beat. A declaration module is configured to declare a VT or SVT based on the comparing operation.

The declaration module may declare a VT when the morphology of the return beat corresponds to the morphology of the BA beat. The arrhythmia module is configured to determine whether the arrhythmia persists following delivery of the ATP therapy. The origin module may determine whether the return beat originates in a ventricle as the reference chamber. The origin module may determine whether the return beat originates in an RA or RV as the reference chamber.

BRIEF DESCRIPTION OF THE DRAWINGS

FIG. 5C illustrates an example of the waveforms that are sensed, compared and classified when an SVT persists and PVCs occur during the arrhythmia following delivery of the ATP therapy.

FIG. 10 illustrates an IMD formed in accordance with an alternative embodiment.

FIG. 11 illustrates an IMD formed in accordance with an alternative embodiment

DETAILED DESCRIPTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Throughout the present application, the term "beat" shall also be used to refer to a waveform for a cardiac event. A beat or cardiac event may begin at any select point during a cardiac cycle and continue until the same select point at the beginning of the next cardiac cycle. For example, a beat may be defined by the waveform extending between successive R waves (e.g., R-R interval), successive P waves (e.g., PP interval) and the like.

Figure 1A:
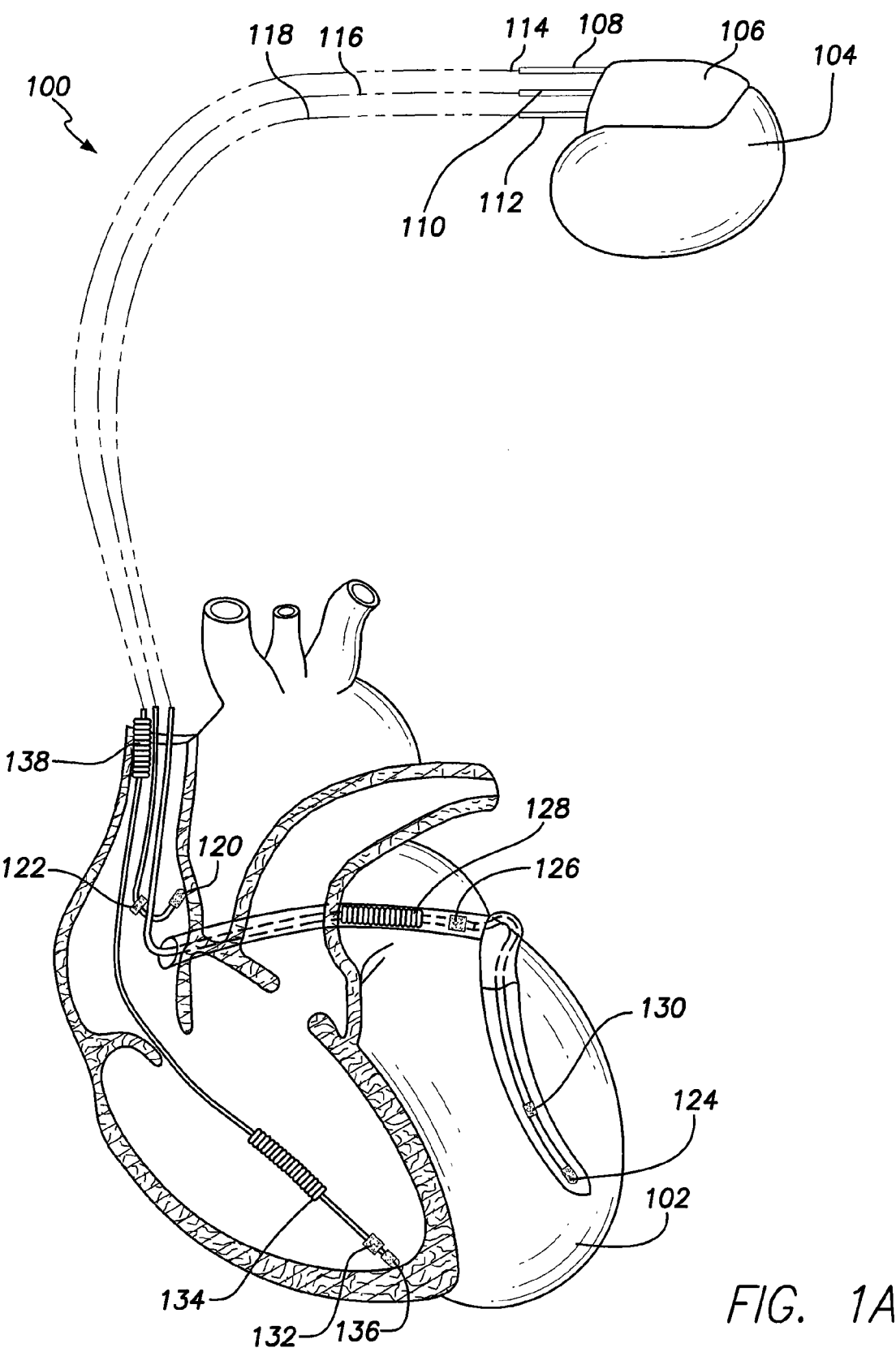
FIG. 1A illustrates an implantable medical device coupled to a heart in a patient and implemented in accordance with one embodiment.

FIG. 1A illustrates an implantable medical device (IMD) 100 implemented in accordance with one embodiment. The IMD 100 may be a cardiac pacemaker, an implantable cardioverter defibrillator (ICD), a cardiac rhythm therapy (CRT) device, a defibrillator, an ICD coupled with a pacemaker, and the like. The IMD 100 may be a dual-chamber stimulation device capable of treating both fast and slow arrhythmias with stimulation therapy, including cardioversion, defibrillation, ATP and pacing stimulation, as well as capable of detecting heart failure, evaluating its severity, tracking the progression thereof, and controlling the delivery of therapy and warnings in response thereto. The IMD 100 may be controlled to sense atrial and ventricular waveforms of interest, discriminate between VT and SVT waveforms of interest, deliver stimulus pulses or shocks, and inhibit application of a stimulation pulse to a heart based on the discrimination between the VT and SVT waveforms of interest and the like. In the example of FIG. 1A, the IMD 100 is located proximate, but external to the heart.

The IMD 100 includes a housing 104 that is joined to a header assembly 106 that holds receptacle connectors 108, 110, 112 connected to lead 114, lead 116, and lead 118, respectively. Embodiments of the present invention may be implemented utilizing all, a pair or only one of the leads 108, 110, and 112. Optionally, embodiments may be implemented utilizing a variety of other, entirely different lead and electrode configurations, provided that electrodes are located in, adjacent, proximate, or at least sufficiently close to the heart to form one or more sensing channels sufficient and capable of detecting cardiac signals associated with one or more beats in a manner discussed herein.

The leads 114, 116, and 118 may include various combinations of electrodes. By way of example only, the lead 116 includes an atrial tip electrode 120 and an atrial ring electrode 122. The lead 118 includes a left ventricular tip electrode 124, a left atrial ring electrode 126, and a left atrial coil electrode 128. The lead 118 also is connected with an LV ring electrode 130 disposed between the LV tip electrode 124 and the left atrial ring electrode 126. The lead 114 has an RV tip electrode 136, an RV ring electrode 132, an RV coil electrode 134, and an SVC coil electrode 138. The leads 114, 116, and 118 deliver therapy and detect IEGM signals from electrical activity over multiple cardiac cycles.

Figure 1B:
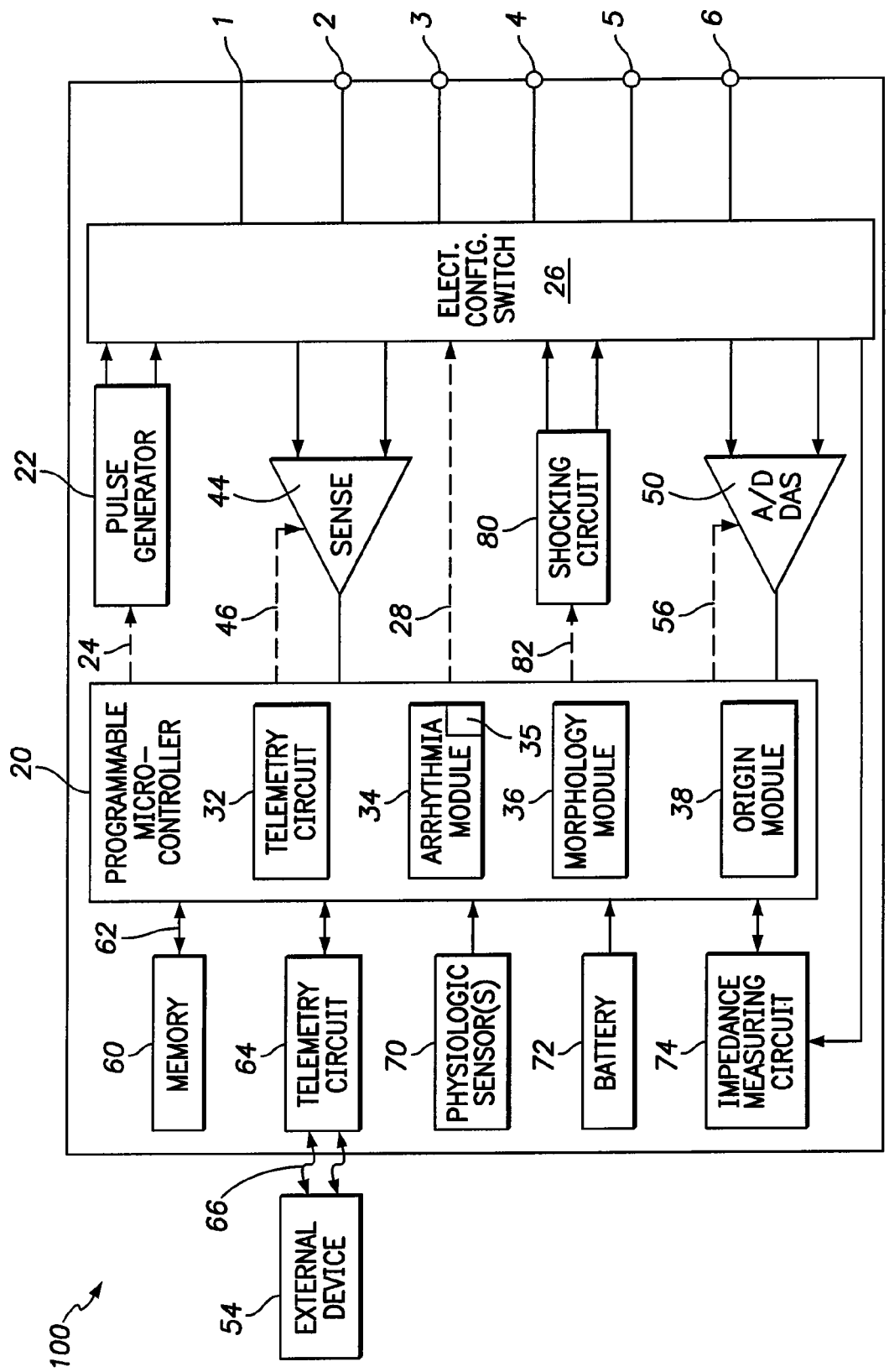
FIG. 1B shows an exemplary IMD 100 that is implanted into the patient.

FIG. 1B shows a block diagram of an exemplary IMD 100 that is implanted into the patient. The IMD 100 may be implemented as a full-function biventricular pacemaker, equipped with both atrial and ventricular sensing and pacing circuitry for one to four chamber sensing and stimulation therapy (including pacing, ATP, and shock treatment). Optionally, the IMD 100 may provide full-function cardiac resynchronization therapy. Alternatively, the IMD 100 may be implemented with a reduced set of functions and components.

The IMD 100 has a housing to hold the electronic/computing components. The housing (which is often referred to as the "can", "case", "encasing", or "case electrode") may be programmably selected to act as the return electrode for certain stimulus and sensing modes. The housing further includes a connector (not shown) with a plurality of terminals 1-6. The terminals 1-6 represent inputs that are configured to receive cardiac signals representative of heart beats sensed over one or more atrial and/or ventricular channels.

The terminals 1-6 may be connected to electrodes that are located in various locations within and about the heart. For example, terminals 1-2 may be coupled to electrodes that form a sensing channel in a first chamber. Terminals 3-4 may be coupled to electrodes that form a sensing channel in a second chamber. The type and location of each electrode may vary. For example, the electrodes may include various combinations of ring, tip, coil and shocking electrodes and the like.

The IMD 100 includes a programmable microcontroller 20 that controls various operations of the IMD 100, including cardiac monitoring and stimulation therapy. Microcontroller 20 includes a processor (or equivalent control circuitry), RAM and/or ROM memory, logic and timing circuitry, state machine circuitry, and I/O circuitry.

IMD 100 further includes a pulse generator 22 that generates stimulation pulses for delivery by one or more electrodes coupled thereto. The pulse generator 22 is controlled by the microcontroller 20 via control signal 24. The pulse generator 22 is coupled to the select electrode(s) via an electrode configuration switch 26, which includes multiple switches for connecting the desired terminals 1-6 and thus electrodes to the appropriate I/O circuits, thereby facilitating electrode programmability. The switch 26 is controlled by a control signal 28 from the microcontroller 20. In the example of FIG. 1B, a single pulse generator 22 is illustrated. Optionally, the IMD 100 may include multiple pulse generators, similar to pulse generator 22, where each pulse generator is coupled to one or more electrodes and controlled by the microcontroller 20 to deliver select stimulus pulse(s) to the corresponding one or more electrodes.

The microcontroller 20 including a timing control circuitry (not shown) to control the timing of the stimulation pulses (e.g., pacing rate, atrioventricular (AV) delay, atrial interconduction (A-A) delay, or ventricular interconduction (V-V) delay, etc.). The timing control circuitry may also be used for the timing of refractory periods, blanking intervals, noise detection windows, evoked response windows, alert intervals, marker channel timing, and so on. Microcontroller 20 also has an arrhythmia module 34 for detecting arrhythmia conditions and a morphology module 36. The arrhythmia module 34 is configured to identify arrhythmias and to determine whether an arrhythmia persists following delivery of a therapy such as an ATP therapy.

The microcontroller 20 is configured to record in memory 60 the cardiac signals associated with waveforms for a predetermined number of beats (e.g., cardiac events), during the arrhythmia. The predetermined number of beats is saved as base arrhythmia (BA) beats or a composite BA beat. The microcontroller 20 also includes a therapy module 32 that is configured to deliver various stimulation pulses as therapies, such as anti-tachy pacing (ATP) therapy, to at least one chamber of the heart. The therapy module 32 may deliver the ATP therapy to both of the RV and RA, both the LA and the LV, both the LV and the RV, and the like. The therapy module 32 may deliver the ATP therapy to a single chamber or multiple chambers. The processor of the microcontroller 20, configured to record in the memory 60, after delivering the ATP therapy, the cardiac signals for at least one return beat. The return beat represents cardiac activity following the ATP therapy. The processor records, as the return beat, the cardiac signal associated with a first intrinsic cardiac event that occurs immediately after completion of the ATP therapy.

An origin module 38 is configured to determine whether the return beat originated in a reference chamber of the heart, or alternatively originated in another chamber. For example, the origin module 38 may determine whether the return beat originates in a ventricle as the reference chamber. The origin module 38 may also determine whether the return beat originates in an RA, LA, RV or LV, any of which may represent the reference chamber.

A morphology module 36 is configured to compare a morphology of the return beat to a morphology of the BA beat. For example, the morphology module 36 is configured to derive the morphology of the BA beat from a series of beats, such as least 3 beats, as the predetermined number of beats. The morphology module 36 may compare a QRJ complex of the return beat and the BA beat. The morphology module 36 compares the return beat sensed over an RA channel to the BA morphology sensed over the RA channel when the return beat originates in the RA. The morphology module 36 is configured to compare at least one of the following, i) shapes of the BA and return beats, ii) a number of peaks in the BA and return beats, iii) an area under curves defined by the BA and return beats, iv) a number of polarity changes in the BA and return beats, and v) a number of positive and negative peaks in the BA and return beats.

The arrhythmia module includes a declaration module 35 that is configured to declare a VT or SVT based on the comparison performed by the morphology module 36. By way of example, the declaration module 35 may be configured to declare a VT when the morphology of the return beat corresponds to the morphology of the BA beat.

The IMD 100 includes sensing circuitry 44 selectively coupled to one or more electrodes that perform sensing operations, through the switch 26 to detect the presence of cardiac activity in the right chambers of the heart. The sensing circuitry 44 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the IMD 100 to sense low amplitude signal characteristics of atrial fibrillation. Switch 26 determines the sensing polarity of the cardiac signal by selectively closing the appropriate switches. In this way, the clinician may program the sensing polarity independent of the stimulation polarity.

The output of the sensing circuitry 44 is connected to the microcontroller 20 which, in turn, triggers or inhibits the pulse generator 22 in response to the absence or presence of cardiac activity. The sensing circuitry 44 receives a control signal 46 from the microcontroller 20 for purposes of controlling the gain, threshold, polarization charge removal circuitry (not shown), and the timing of any blocking circuitry (not shown) coupled to the inputs of the sensing circuitry.

In the example of FIG. 1B, a single sensing circuit 44 is illustrated. Optionally, the IMD 100 may include multiple sensing circuit, similar to sensing circuit 44, where each sensing circuit is coupled to one or more electrodes and controlled by the microcontroller 20 to sense electrical activity detected at the corresponding one or more electrodes. The sensing circuit 44 may operate in a unipolar sensing configuration or in a bipolar sensing configuration.

The IMD 100 further includes an analog-to-digital (A/D) data acquisition system (DAS) 50 coupled to one or more electrodes via the switch 26 to sample cardiac signals across any pair of desired electrodes. The data acquisition system 50 is configured to acquire intracardiac electrogram signals, convert the raw analog data into digital data, and store the digital data for later processing and/or telemetric transmission to an external device 54 (e.g., a programmer, local transceiver, or a diagnostic system analyzer). The data acquisition system 50 is controlled by a control signal 56 from the microcontroller 20.

The microcontroller 20 is coupled to the memory 60 by a suitable data/address bus 62. The programmable operating parameters used by the microcontroller 20 are stored in memory 60 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the IMD 100 may be non-invasively programmed into the memory 60 through a telemetry circuit 64 in telemetric communication via communication link 66 with the external device 54. The telemetry circuit 64 allows intracardiac electrograms and status information relating to the operation of the IMD 100 (as contained in the microcontroller 20 or memory 60) to be sent to the external device 54 through the established communication link 66. The IMD 100 can further include magnet detection circuitry (not shown), coupled to the microcontroller 20, to detect when a magnet is placed over the unit. A magnet may be used by a clinician to perform various test functions of the IMD 100 and/or to signal the microcontroller 20 that the external programmer 54 is in place to receive or transmit data to the microcontroller 20 through the telemetry circuits 64.

The IMD 100 can further include one or more physiologic sensors 70. Such sensors are commonly referred to as "rate-responsive" sensors because they are typically used to adjust pacing stimulation rates according to the exercise state of the patient. However, the physiological sensor 70 may further be used to detect changes in cardiac output, changes in the physiological condition of the heart, or diurnal changes in activity (e.g., detecting sleep and wake states). Signals generated by the physiological sensors 70 are passed to the microcontroller 20 for analysis. The microcontroller 20 responds by adjusting the various pacing parameters (such as rate, AV Delay, V-V Delay, etc.) at which the atrial and ventricular pacing pulses are administered. While shown as being included within the IMD 100, the physiologic sensor(s) 70 may be external to the IMD 100, yet still be implanted within or carried by the patient. Examples of physiologic sensors might include sensors that, for example, sense respiration rate, pH of blood, ventricular gradient, activity, position/posture, minute ventilation (MV), and so forth.

A battery 72 provides operating power to all of the components in the IMD 100. The battery 72 is capable of operating at low current drains for long periods of time, and is capable of providing high-current pulses when the patient requires a shock pulse (e.g., in excess of 2 A, at voltages above 2 V, for periods of 10 seconds or more). The battery 72 also desirably has a predictable discharge characteristic so that elective replacement time can be detected. As one example, the IMD 100 employs lithium/silver vanadium oxide batteries. The IMD 100 further includes an impedance measuring circuit 74, which can be used for many things. The impedance measuring circuit 74 is coupled to the switch 26 so that any desired electrode may be used.

The microcontroller 20 controls a shocking circuit 80 by way of a control signal 82. The shocking circuit 80 generates shocking pulses of low (e.g., up to 0.5 joules), moderate (e.g., 0.5-10 joules), or high energy (e.g., Z11 to 40 joules), as controlled by the microcontroller 20. It is noted that the shock therapy circuitry is optional and may not be implemented in the IMD.

Figure 2A:
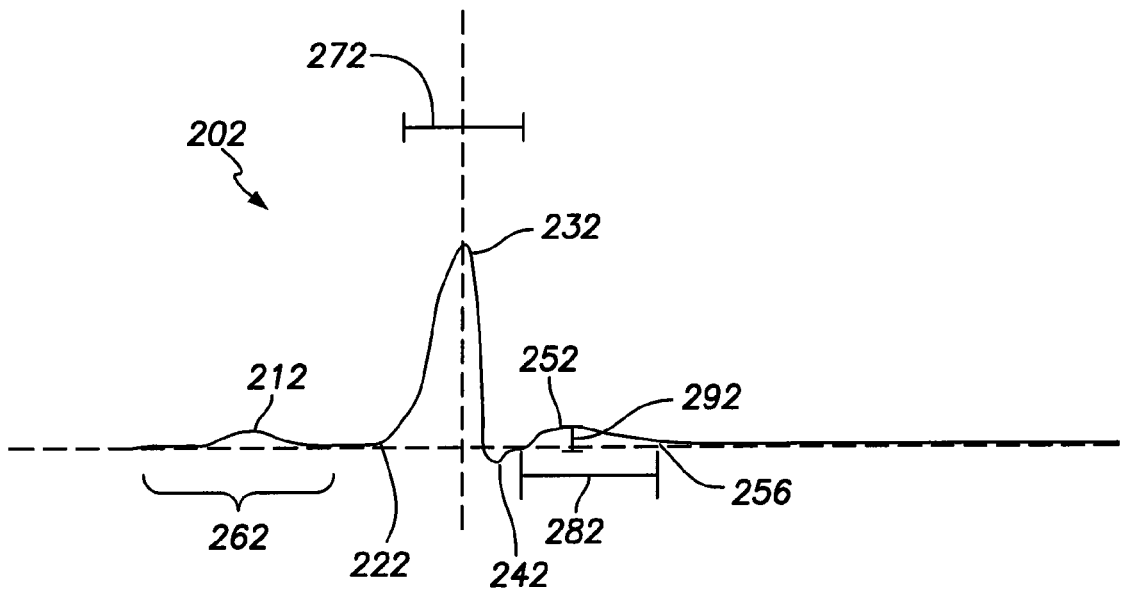
FIGS. 2A and 2B illustrates examples of waveforms obtained at different times during sensing over one or more sensing channels.
Figure 2B:
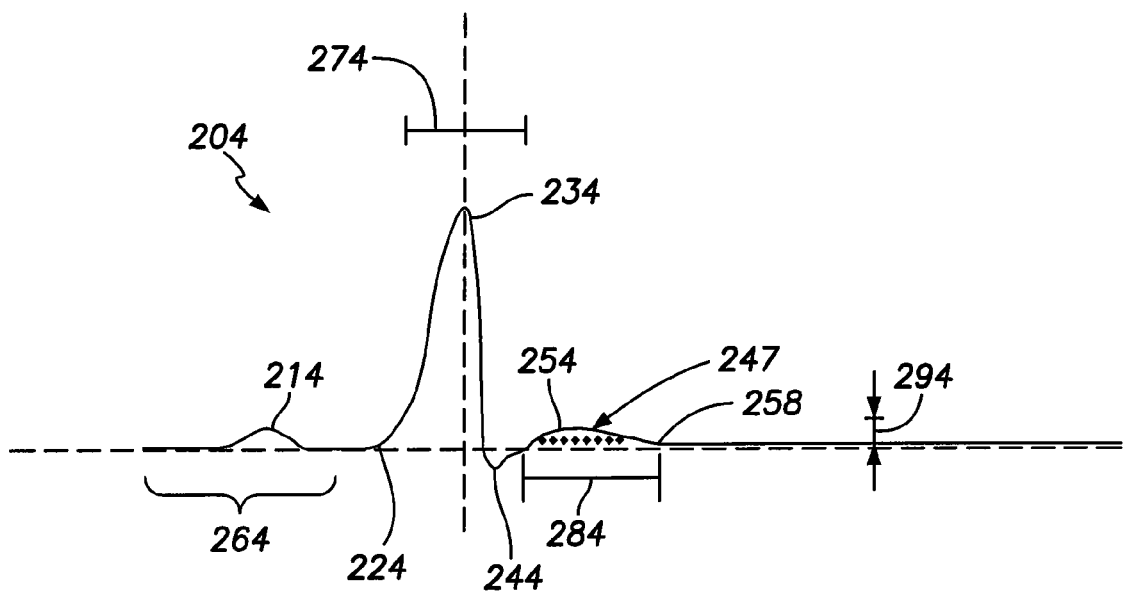

FIGS. 2A and 2B illustrates examples of waveforms obtained at different times during sensing over one or more sensing channels. FIG. 2A represent a baseline waveform or BA beat 202 collected during an arrhythmia prior to delivery of an ATP therapy, while FIG. 2B represents a post-therapy return beat 204 collected after delivery of an ATP therapy. FIGS. 2A-2B include horizontal time axes and vertical axes that define units in voltage. The shapes of the waveforms 202, 204 will vary based upon the heart behavior, electrode combination and the like. The waveforms 202, 204 include P-waves 212, 214, Q-waves 222, 224, R-waves 232, 234, S-waves 242, 244, and T-waves 252, 254. The P-waves 212, 214 represent atrial depolarization and may be used to characterize atrial activity of the heart. The R-waves 232, 234 represent ventricular depolarization and may be used to characterize ventricular activity of the heart 102. The T-waves 252, 254 represent the relaxation or repolarization of the heart.

As explained below, portions of the waveforms or beats 202, 204 are analyzed for various features of interest. Each waveform or beat 202, 204 may be segmented into P-wave zones 262, 264, R-wave zones 272, 274 and ST-segment zones 282, 284. The portions of the waveforms 202, 204 within each zone 262, 264, 272, 274, 282, 284 are analyzed for different features of interest.

The zones 262, 264, 272, 274, 282, 284 are established about the QRS complex of each waveform 202, 204. Each zone 262, 264, 272, 274, 282, 284 may extend, by predetermined and/or programmed time periods, upstream (before) and downstream (after) from the peak of the corresponding R-waves 232, 234. The peak of the R-wave 232, 234 may be used to scale the waveforms 202, 204 to a common scale.

The zones 262, 264 are established to represent regions where the P-waves 212, 214 are located. Each zone 262, 264 may be defined to have a predetermined or programmed length. Each zone 262, 264 may be positioned along the corresponding waveform 202, 204 by centering (or otherwise positioning) the zone 262, 264 at the peak of the P-wave 212, 214. Alternatively, the zone 262, 264 may be positioned by setting the beginning of the zone 262, 264 a predetermined or programmed time period before the peak of the corresponding R-wave 232, 234 or a predetermined or programmed time period before the beginning of the corresponding zone 272, 274. The portions of the waveforms 202, 204 in the zones 262, 264 are analyzed to establish the isoelectric level. The isoelectric level in each waveform 202, 204 is used to align waveforms 202, 204 with one another.

The ST-segment zones 282, 284 include ST-segment durations that begin immediately after the zones 272, 274 and continue until the corresponding waveform 202, 204 crosses the zero voltage level which is denoted as the neutral crossing point 256, 258. The ST-segment zones 282, 284 include corresponding maximum ST-segment shifts 292, 294 that extend from the horizontal axis (which represents the zero voltage level) up to the peak of the T-wave 252, 254. As shown in FIG. 2B, the ST-segment zone 284 include an area 247 under the corresponding portion of the waveform 204 that may be utilized as a characteristic of interest in BA and return beats.

Optionally, the isoelectric leveling may correspond to a minimum or average level of the PQ segment within the isoelectric zone 262, 264. Optionally, the isoelectric level may correspond to a level in the BA or return beats 202, 204 measured at a predetermined time following the peak of the P-wave 212, 214. As a further example, the isoelectric level may correspond to a level in the BA or return beats 202, 204 that is measured a predetermined time before the peak of the P-wave 212, 214. In one embodiment, a separate isoelectric level is identified for each BA beat and a separate isoelectric level is identified for each return beat. Alternatively, a cumulative isoelectric level may be formed based on a group of BA beats.

Figure 3:
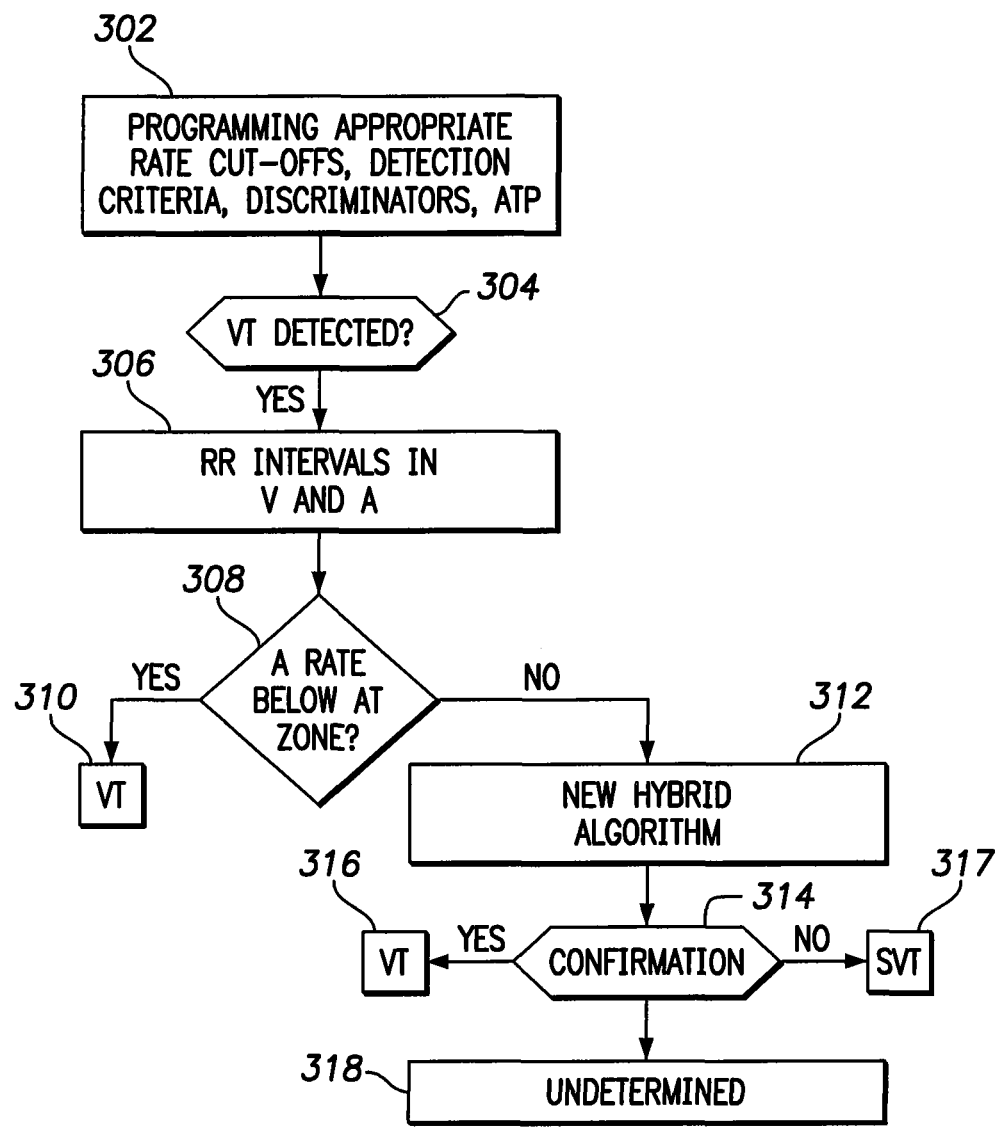
FIG. 3 illustrates a flow chart for a process performed in accordance with an embodiment for identifying arrhythmias.

FIG. 3 illustrates a flow chart for a process performed in accordance with an embodiment for identifying arrhythmias. Beginning at 302, the method permits the physician or programmer to program appropriate physiologic parameters and IMD parameters, such as rate cut-offs, detection criteria discriminators, ATP therapies and the like. At 304, the method determines whether a high ventricular rate is detected (e.g., greater than 100). At 306, the method identifies the RR interval in the ventricle and the PP interval in the atrium. At 308, the method determine whether the PP interval is below an AT zone threshold (set at 302). For example, if the AT zone rate cut-off is 150, then at 308 the method determines whether the PP interval exceeds the AT zone rate cut-off. If the PP interval exceeds the AT zone rate cut-off, then VT may be declared at 310. When the PP interval is below the AT zone rate cut-off, then flow moves to 312.

At 312 a method is implemented in accordance with an embodiment for discriminating heart arrhythmias (as explained hereafter). At 314, optionally, a confirmation operation may be performed to confirm the determination made at 312. Optionally, 314 may be omitted. Next, flow moves to 316-318. At 316, VT is confirmed and VT related operations are performed by the IMD, such as delivery of a therapy, recording physiologic information regarding the VT, and the like. At 317, SVT is confirmed and SVT related operations are performed by the IMD, such as delivery of a therapy, recording physiologic information regarding the SVT, and the like. At 318, an "undetermined" declaration is confirmed and related operations are performed by the IMD, such as recording physiologic information regarding the undeclared events, and the like.

Figure 4A:
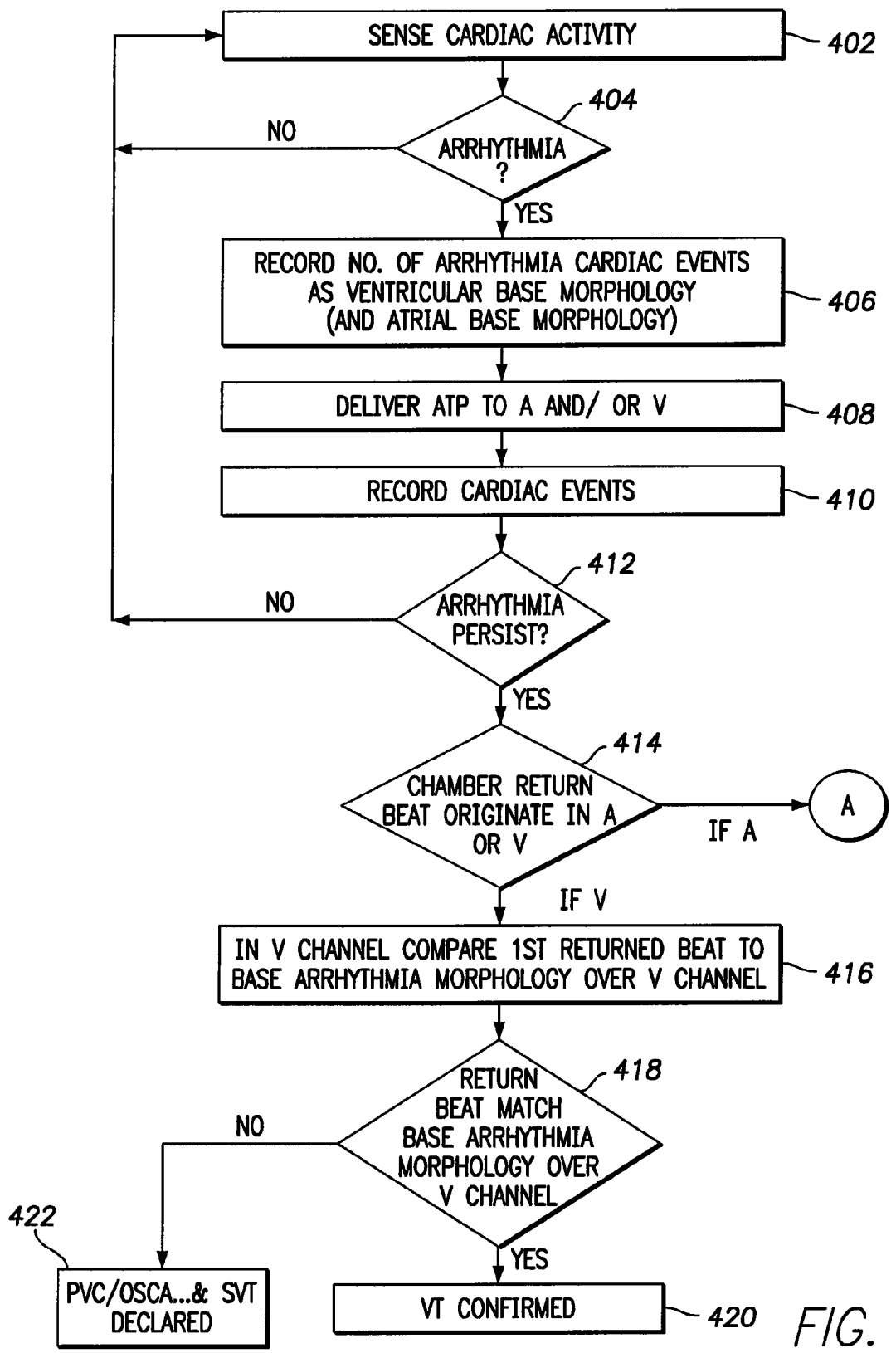
FIGS. 4A and 4B illustrate a method performed in accordance with an embodiment for discriminating heart arrhythmias.
Figure 4B:
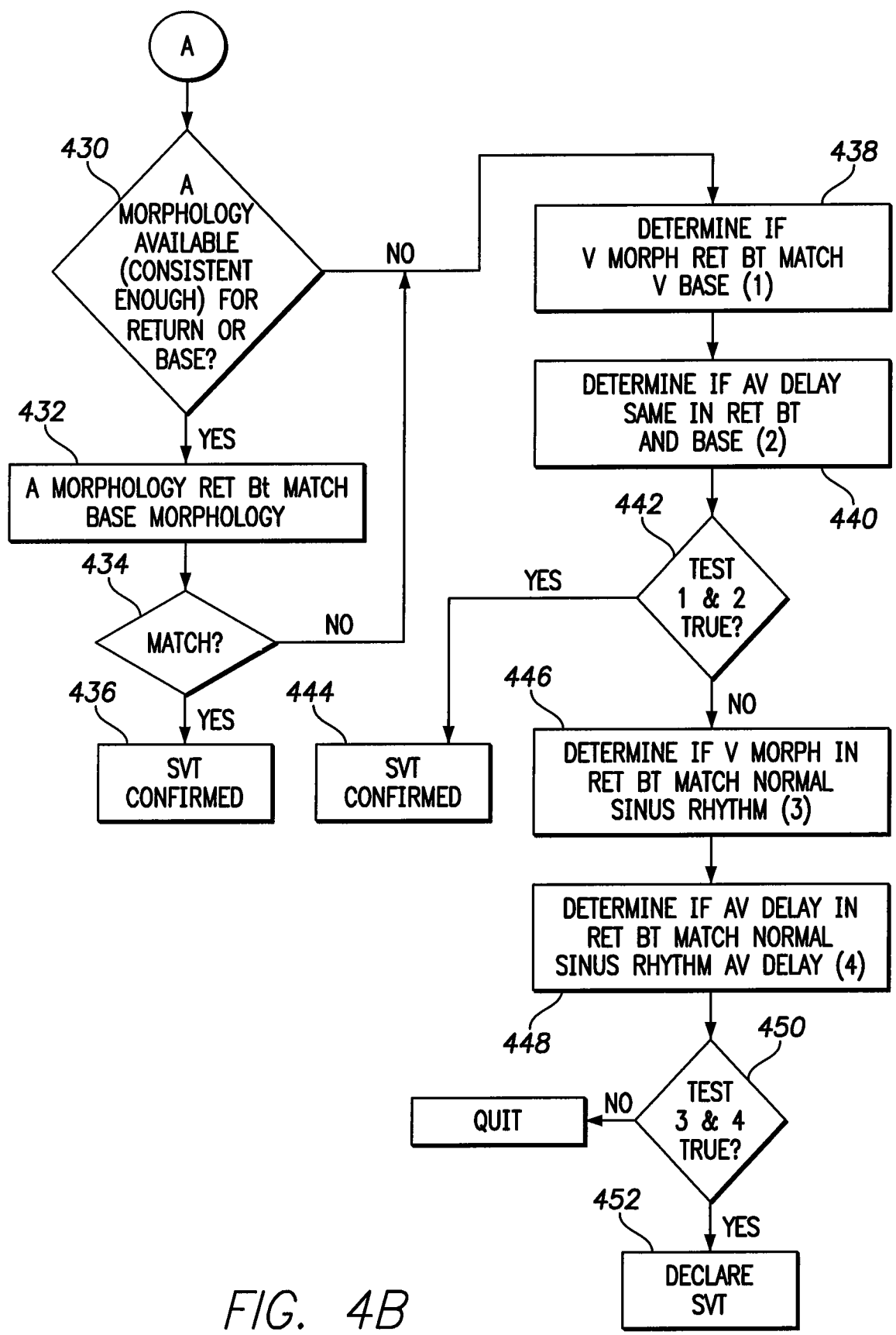

FIGS. 4A and 4B illustrate a method performed in accordance with an embodiment for discriminating heart arrhythmias. The method may be implemented by an IMD or an external programmer device and the like. The method of FIG. 4 senses cardiac signals, associated with cardiac events or beats, over one or more sensing channels. Beginning at 402, the method senses cardiac events over one or both of the atrial and/or ventricular sensing channels. For example, the sensed cardiac signals, associated with atrial activity, may be collected over an atrial sensing channel, such as between one or more electrodes located in or near the atrial chamber of interest (e.g. RA or LA). Optionally, or in addition, the sensed cardiac signals, associated with ventricular activity, may be collected over a ventricular sensing channel, such as between one or more electrodes located in or near the ventricular chamber of interest (e.g. RV or LV). Alternatively, sensing channels may be defined between combinations of 2, 3, 4 or more electrodes located in various chambers of the heart as well as outside the heart, including the use of the IMD housing as a sensing electrode.

At 404, the method analyzes the cardiac event signals to determine whether an arrhythmia of interest is occurring. By way of example, the arrhythmia of interest may represent various forms of tachyarrhythmias, such as VT, SVT and the like. The arrhythmia may be detected from cardiac signals sensed over the atrial sensing channel and/or cardiac signals sensed over the ventricular sensing channel.

At 406, when an arrhythmia of interest is identified, the method begins to record cardiac signals over a ventricular sensing channel (V channel) and continues recording for a predetermined number of cardiac cycles. Optionally, at 406 cardiac signals may also be recorded over an atrial sensing channel (A channel) for a predetermined number of cardiac cycles. At 406, cardiac signals for one or more cardiac cycles are recorded during the arrhythmia and stored in memory as V and A base arrhythmia (BA) beats. The cardiac signals over the V and A channels define the morphology for the V and A base arrhythmias, respectively. The V and A morphologies may be derived from one, two or a series of at least 3 beats. For example, the ventricular and atrial components of the cardiac signal for one beat during the arrhythmia may be stored in memory 60 as V and A base arrhythmia beats, respectively. Optionally, the ventricular and atrial components of the cardiac signals for two or more beats may be stored separately in memory 60 as a series of V and A base arrhythmia beats, respectively. Alternatively, the V components of cardiac signals for multiple beats may be combined, such as through averaging or another combining method, to form a composite V base arrhythmia beat. Similarly, A components of multiple beats may be combined to form a composite A base arrhythmia beat.

At 408, the method delivers anti-tachy pacing (ATP) therapy to at least one chamber of the heart. For example, the method may deliver the ATP therapy to both of the RV and RA, both the LV and LA, the LV and RV, etc. Alternatively, the method may deliver the ATP therapy to one chamber such as the RA, or only to another chamber such as the RV. Optionally, the ATP therapy may be delivered to the LV and/or LA.

At 410, after delivering the ATP therapy, the method records cardiac signals, over one or more sensing channels in at least a reference chamber of the heart, for at least one return beat. The reference chamber may represent a chamber in which cardiac activity, associated with a single cardiac event, originates during normal physiologic behavior. Alternatively, the reference chamber may represent a chamber in which cardiac activity, associated with a single cardiac event, originates during abnormal pathologic behavior. The return beat(s) represent cardiac activity following delivery of the ATP therapy. The return beat or beats represents a first intrinsic cardiac event that occurs immediately after completion of the ATP therapy. The cardiac signals for the return beats may be sensed utilizing electrodes located in the atrium and/or ventricle.

As one example, one set of electrodes in the atrium may be configured to perform near field sensing to define an atrial sensing channel, while another set of electrodes in the ventricle may be configured to perform near field sensing to define a ventricular sensing channel. Optionally, electrodes in the atrium may be configured to perform far field sensing to define the ventricular sensing channel. Optionally, electrodes in the ventricle may be configured to perform far field sensing to define the atrial sensing channel. Optionally, the atrial and/or ventricular sensing channels may be defined between a combination of electrodes in an atrium and electrodes in a ventricle. Once one or more return beats are recorded and stored in memory 60, flow moves to 412.

At 412, the method analyzes one or more cardiac events following delivery of the ATP therapy and determines whether the arrhythmia persists. For example, the return beat(s) recorded at 410 may be analyzed to determine whether the heart rate is still elevated. Optionally, cardiac signals following the return beat(s) may be analyzed alone or in combination with the return beat(s) to determine whether the arrhythmia persists. The cardiac signals at 412 may be analyzed based on rate along, or based on more complex algorithms, alone or in combination with rate, to determine whether the heart is still exhibiting an arrhythmia. If no arrhythmia persists at 412, the method exits and returns to the starting point to monitor for arrhythmias. If an arrhythmia persists at 412, flow moves to 414.

At 414, the method determines in which chamber of the heart, the return beat or beats originated. The return beats represent intrinsic (normal or abnormal) cardiac activity that begins at an originating point in the heart. The originating point may vary depending upon the type of arrhythmia. For example, cardiac activity associated with VT may begin at an originating point in the conductive tissue of the RV (or LV). Alternatively, the cardiac activity associated with SVT may begin at an originating point in the conductive tissue of the, SVC, RA (or LA), SA node and the like. As one example, the determining operation at 414 may determine whether the return beat originates in the RA or RV as the reference chamber. As another example, the determining operation may determine whether the return beat originates in an RA or LA as the reference chamber. As a further example, the determining operation may determine whether the return beat originates in an RV or LV, or in the LA or LV as the reference chamber.

At 414, the method determines the chamber of original based on an approximate point of origin for the return beat. The determination may be based on various criteria and/or algorithms. Optionally, the point of origin of the return beat may be determined to correspond to the first chamber in which intrinsic cardiac activity is sensed following ATP therapy. For example, cardiac signals detected over the atrial and ventricular sensing channels may be compared to determine which channel first detects a signal having a magnitude that exceeds one or more predetermined thresholds. For example, an atrial threshold and a separate ventricular threshold may be defined. Cardiac signals sensed over the atrial channel may then be compared to the atrial threshold, while cardiac signals sensed over the ventricular channel may then be compared to the ventricular threshold. The one of the atrial and ventricular channels, that first detect a cardiac signal that exceeds the corresponding atrial and ventricular threshold, may be declared to represent to the chamber in which the return beat originated.

Optionally, the point of origin may be determined based on delays between when multiple electrodes sense cardiac activity. For example, the electrodes on a quad-pole lead sense cardiac activity at different points in time associated with a single event. The timing and delays may be used to calculate an approximate point of origin for the event.

Once the point of origin is approximated, the method determines the chamber of origin for the return beat. The chamber of origin may be the reference chamber or an adjacent chamber. For example, when the reference chamber is the RA, the chamber of origin may be the RA or RV. Any chamber may represent the chamber of origin. For example, the RV, LA or LV may also be the chamber of origin. The method utilizes the chamber of origin to select the sensing channel from which the base arrhythmia and return beats should be compared. At 414, when it is determined that the RV is the chamber of origin, flow moves to 416. When it is determined that the RA is the chamber of origin, flow moves to point (A) in FIG. 4B. At 416, once the chamber of origin for the return beat(s) are identified as the RV, the method compares morphology of the RV return beat to morphology of a RV BA beat as sensed over one or more RV sensing channels. The comparing operation may include comparing a QRS complex of the return beat and the QRS complex of the BA beat, comparing a magnitude of the R-wave peak of the return beat and the magnitude of the R-wave peak of the BA beat, and the like. Each comparing operation in general compares cardiac signals sensed at different times over a common channel.

Optionally, the method need not be limited to comparison of cardiac signals sensed over one RV channel. For example, when the BA beat and the return beat are recorded over each of LV and RV channels, BA and return beats from the LV channel may be compared and BA and return beats from the RV channel may also be compared. Also, more than one sensing channel may be defined in the RV and/or in the LV. When multiple RV sensing channels are defined, the cardiac signals (corresponding to the BA beats) sensed over each of the RV sensing channels may be compared with cardiac signals (corresponding to the return beats) sensed over the same RV sensing channels.

Optionally, the comparing operation may include at least one of the following: i) comparing shapes of the BA and return beats, ii) comparing a number of peaks in the BA and return beats, iii) comparing an area under curves defined by the BA and return beats, iv) comparing a number of polarity changes in the BA and return beats, and v) comparing a number of positive and negative peaks in the BA and return beats. Optionally, the comparing operation may compare alternative features and characteristics of the BA and return beats.

At 418, the method determines whether the BA and return beats for the RV are sufficiently similar to be declared a match. A match may exist when a sufficient degree of correlation exist, the number of BA to return beats peaks are close or equal, the number of BA and return beat polarity changes are close or equal, and the like. When a match exists, flow moves to 420, otherwise, flow moves to 422. A VT is declared at 420 when a ventricle is the chamber or origin for the return beat and the morphology of the V channel return beat corresponds to the morphology of the V channel BA beat. At 422, the method may declare an SVT. The declaring operations at 420 and 422 may declare the VT or SVT based solely on the comparison in 416. Optionally, the VT or SVT may be declared based in part on the comparison in 416, and in part on other factors, such as atrial rate, ventricular rate, AV dissociation, and the like.

Returning to 414, when the chamber of origin is an atrium, flow moves to FIG. 4B, point 430. At 430, it is determined whether the A channel collected cardiac signals associated with BA and/or return beats that have sufficiently consistent or reliable morphology to be utilized. For example, if the A channel collects BA beats that have a morphology with large variation or inconsistent shape, the BA beats may be classified as unreliable and thus not available for comparison at 430. Similarly, the A channel may collect return beats that have morphology with large variation or inconsistent shape. Thus, the return beats could be classified as unreliable and not available to use at 430. If the A channel BA and return beats are available, flow moves to 432; otherwise, flow moves to 438.

At 432, when the return beat originates in the RA, the comparing operation compares the morphology of the return beat(s) sensed over the RA channel to the morphology of a BA beat(s) sensed over the same RA channel to determine whether a match exists. When the RA is the chamber of origin, the comparing operation may represent a comparison of the P-waves during the BA and return beats.

At 434, it is determined whether the BA and return beats, over the A channel, are sufficiently close or similar to declare a match. When a match exists, flow moves to 436; otherwise flow moves to 438. At 436, an SVT is declared.

The operations at 438-450 represent a surrogate process that seeks to determine whether an SVT exists, given that BA and return beats were not collected over an A channel with sufficient reliability to compare. At 438, it is determined whether the morphology of the Ba and return beats, as measured over the V channel match are sufficiently similar to declare a match (labeled "test(1)").

At 440, it is determined whether the AV delay associated with the BA beats matches the AV delay associated with the return beats (labeled "test(2)").

At 442, it is determined whether the tests (1) and (2) at 438 and 440 are both true. If the tests (1) and (2) at both of 438 and 440 are true, an SVT is declared at 444. If one or both of the tests at 438 and 440 are false, flow moves to 446. At 446, it is determined whether the morphology of the return beat as measured over the V channel matches the morphology of a normal sinus rhythm measured over the V channel. At 448, it is determined whether the AV delay associated with the return beats matches the AV delay associated with a normal sinus rhythm. At 450, it is determined whether the tests at 446 and 448 are both true, and if so, flow moves to 452 where an SVT is declared. Otherwise, the process ends without declaring an SVT or VT.

The foregoing process is described in connection with the RA and RV. However, optionally, the process may be implemented in connection with other combination of heart chambers, such as the LA and LV, RV and LV, RA and LA. Optionally, the process may be used with more than two chambers. For example, the collection and comparison of AV delay, BA and return beats of FIG. 4 for the RA may be performed for the RA and LA, while the collection and comparison of BA, return beats, AV delays for the RV may be performed for the RV and LV.

As explained above, the method of FIG. 4, affords a hybrid process with static and dynamic aspects to afford rhythm discrimination. The static aspects include delivery of ATP therapy in an atrial chamber and/or in a ventricular chamber. The dynamic aspects include comparing features and/or characteristics of the morphologies for the BA and return beats such that the method does not mischaracterize VTs or SVTs. For example, the comparison is well suited to properly characterize VTs and SVTs, even when PVCs or PACs occur, or when oscillations or aberrations in the cardiac activity occur at the end of an ATP therapy. The method of FIG. 4 affords higher specificity by removing the effects of PVCs, PACs, and oscillations or aberrations at the end of ATP therapy. Further, the method of FIG. 4 avoids the need to store baseline templates for morphology comparison because, among other things, the comparison of morphologies are made between recordings of several beats (BA and return) that occur during and after the arrhythmia (before and after the ATP therapy).

Figure 5A:
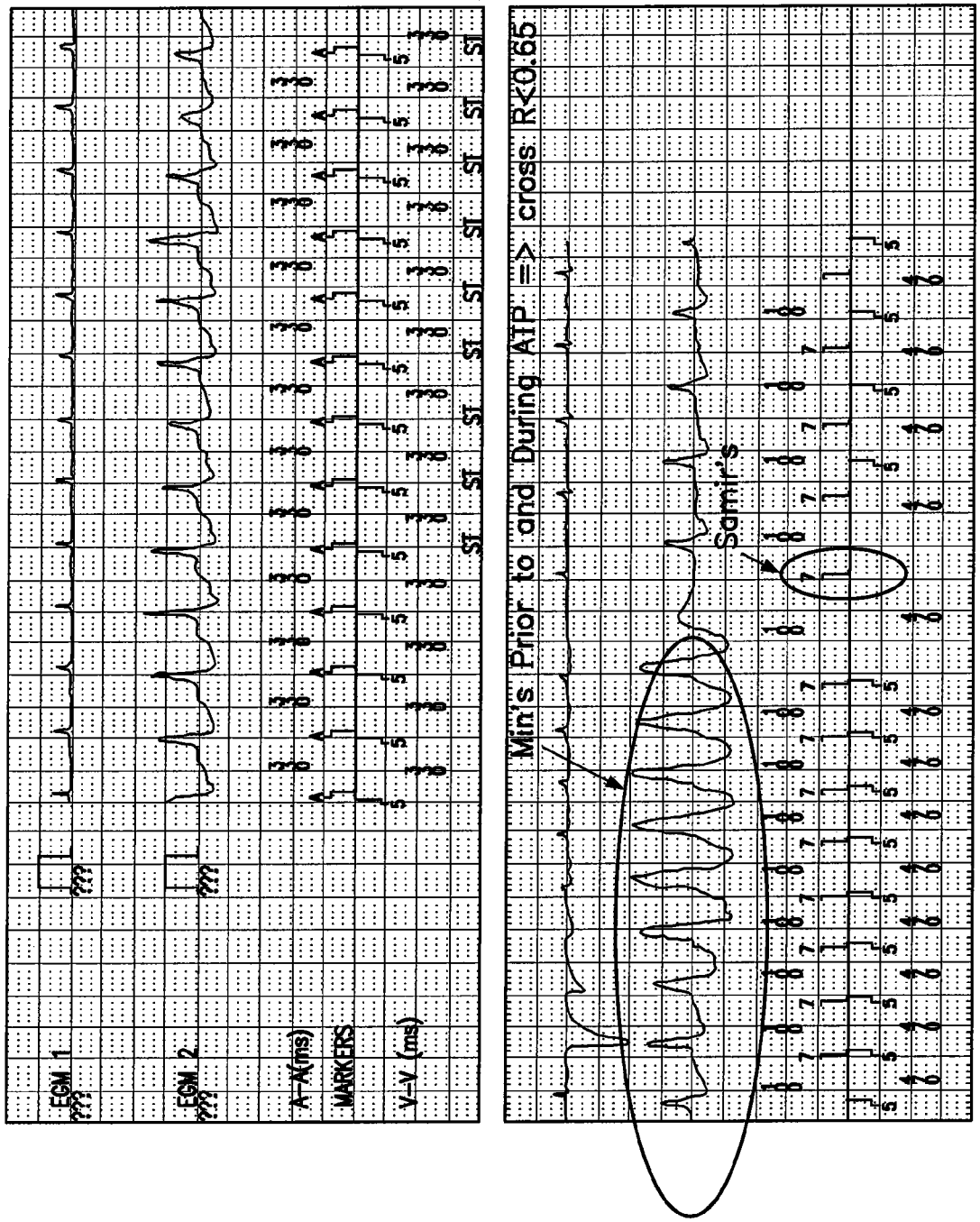
FIG. 5A illustrates an example of the waveforms that are sensed, compared and classified when an SVT persists following ATP therapy.
Figure 5B:
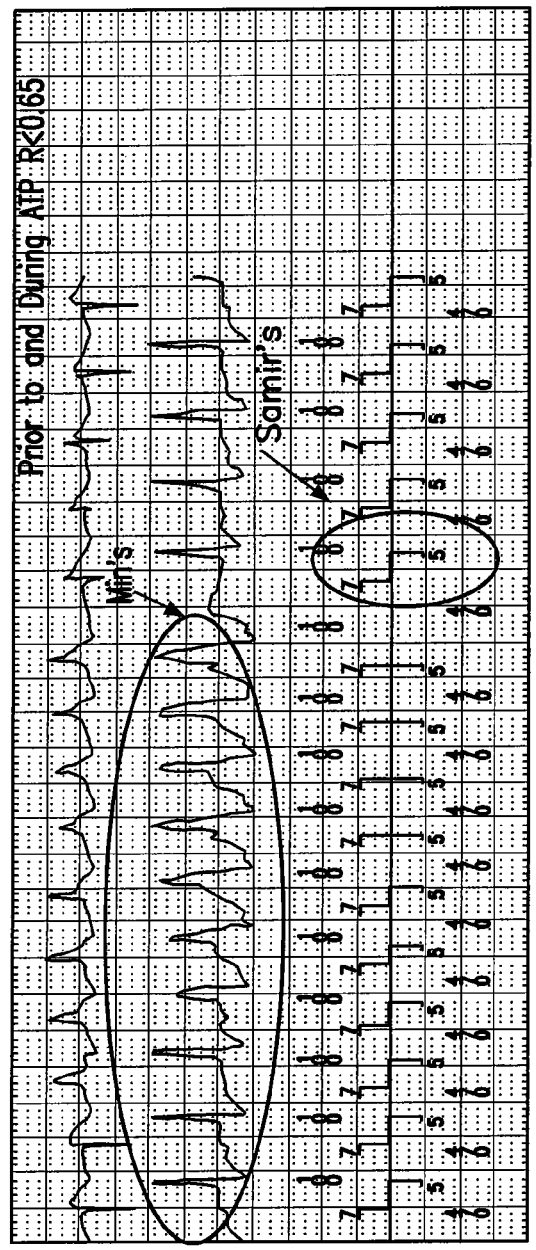
FIG. 5B illustrates an example of the waveforms that are sensed, compared and classified when an SVT is terminated by the ATP therapy.
Figure 5D:
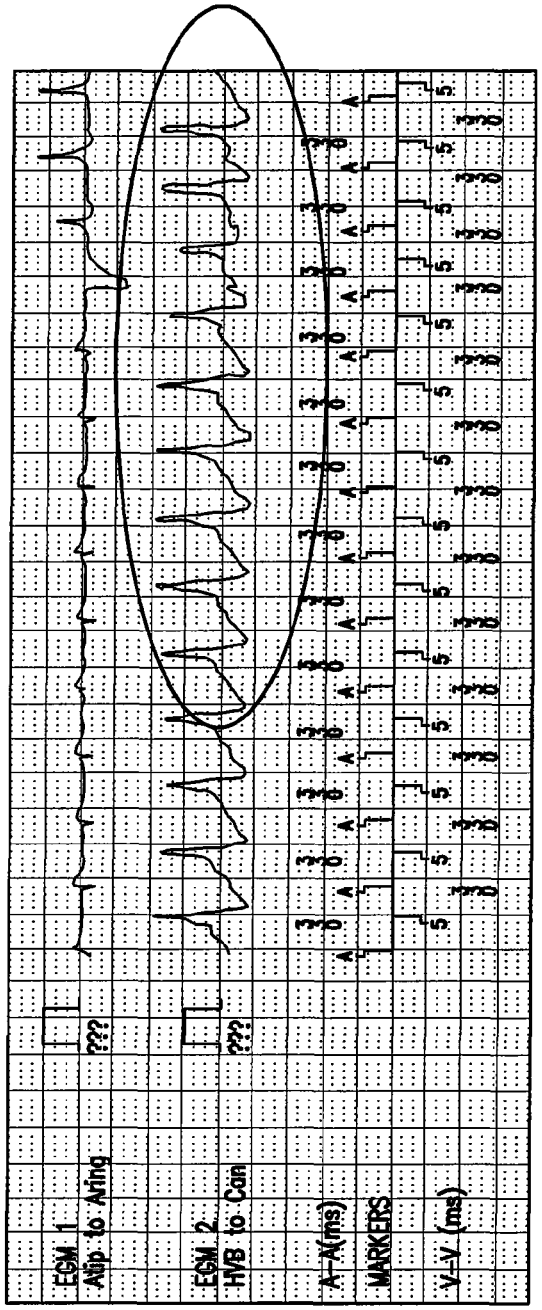
FIG. 5D illustrates an example of the waveforms that are sensed, compared and classified when a VT is terminated by the ATP therapy.
Figure 5D:
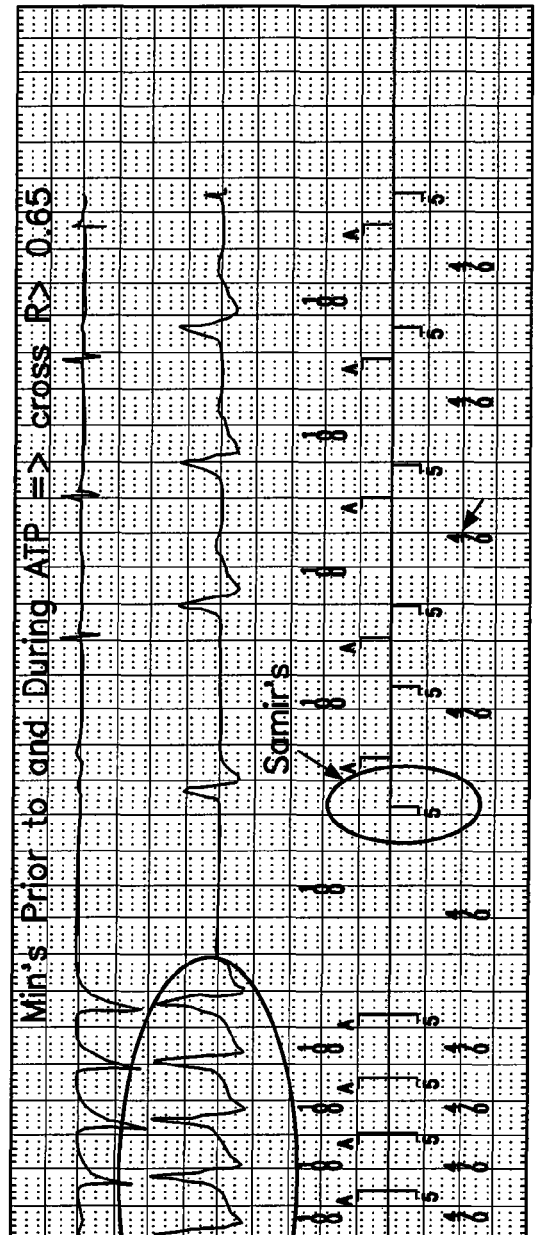

FIGS. 5A-5D illustrate examples of waveforms collected over various atrial and/or ventricular sensing channels while experiencing an arrhythmia before and after ATP therapy. FIG. 5A illustrates an example of the waveforms that are sensed, compared and classified when an SVT persists following ATP therapy. FIG. 5B illustrates an example of the waveforms that are sensed, compared and classified when an SVT is terminated by the ATP therapy. FIG. 5C illustrates an example of the waveforms that are sensed, compared and classified when an SVT persists and PVCs occur during the arrhythmia following delivery of the ATP therapy. FIG. 5D illustrates an example of the waveforms that are sensed, compared and classified when an VT is terminated by the ATP therapy.

Figure 6:
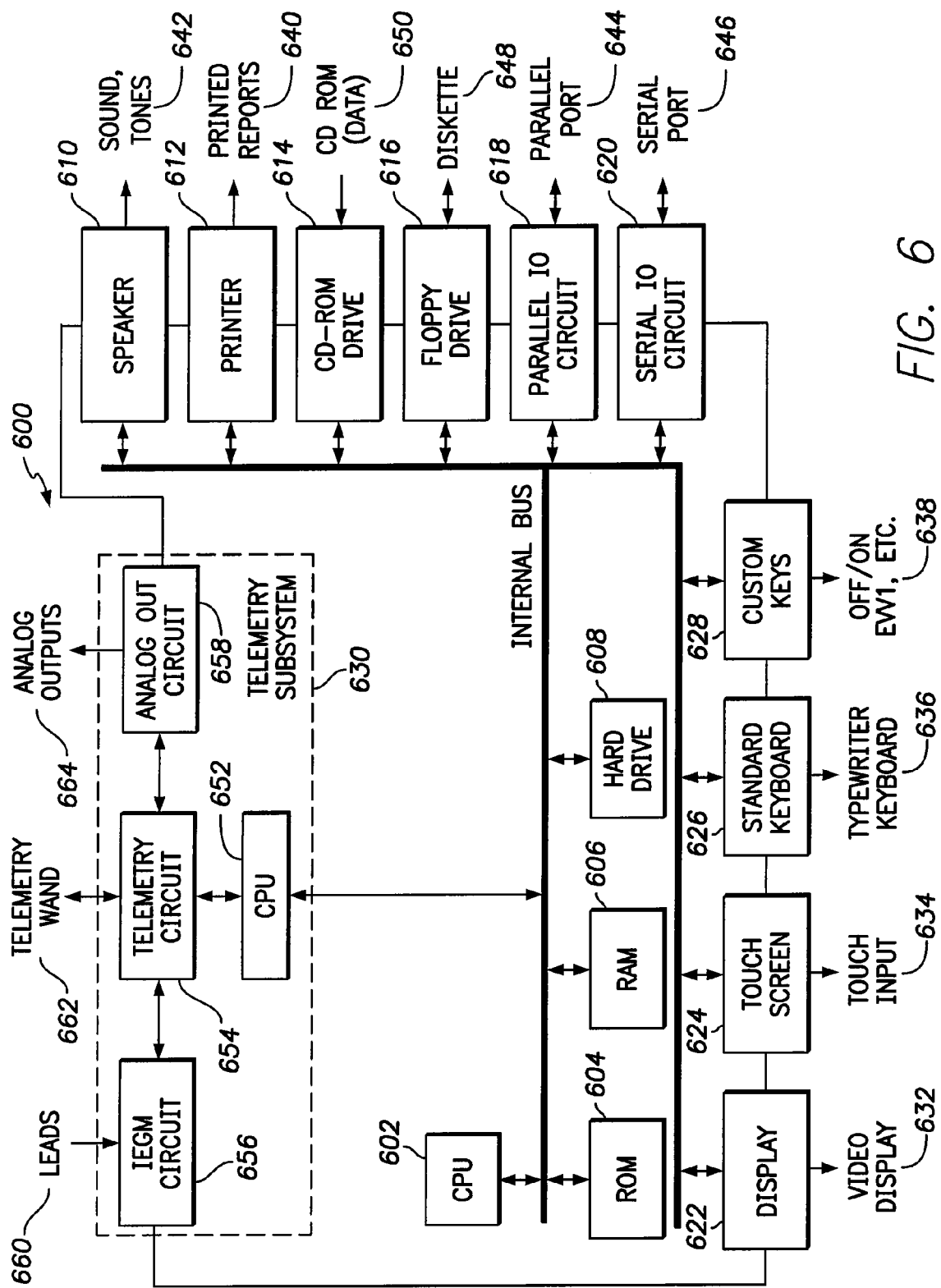
FIG. 6 illustrates a functional block diagram of the external device that is operated in accordance with the processes described herein and to interface with implantable medical devices as described herein.

FIG. 6 illustrates a functional block diagram of an external device 600 that is operated in accordance with the processes described herein and to interface with implantable medical devices as described herein. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630.

The CPU 602 performs the process discussed above. The CPU 602 may include RAM or ROM memory, logic and timing circuitry, state machine circuitry, and I/O circuitry to interface with the IMD 100. The display 622 (e.g., may be connected to the video display 632). The touch screen 624 may display graphic information relating to the IMD 100. The display 622 displays various types of information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the external device 600, wirelessly to the telemetry subsystem 630 input.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 600 to the IMD 100.

Figure 7:
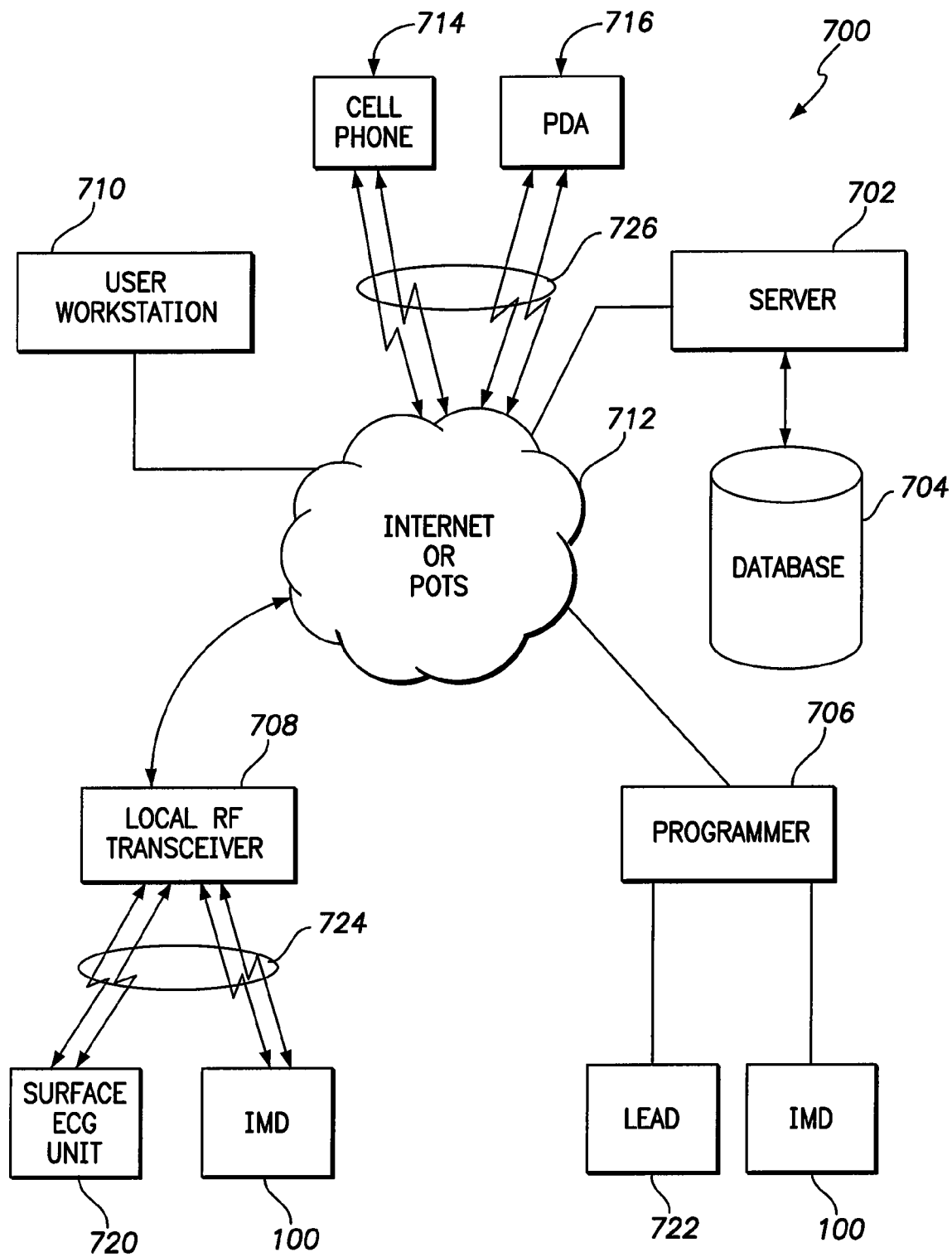
FIG. 7 illustrates a distributed processing system in accordance with one embodiment.

FIG. 7 illustrates a distributed processing system 700 in accordance with one embodiment. The distributed processing system 700 includes a server 702 connected to a database 704, a programmer 706, a local RF transceiver 708 and a user workstation 710 electrically connected to a communication system 712. Any of the processor-based components in FIG. 7 (e.g., workstation 710, cell phone 714, PDA 716, server 702, programmer 706, IMD 100) may perform the COI measurement process discussed above.

The communication system 712 may be the internet, a voice over IP (VoIP) gateway, a local plain old telephone service (POTS) such as a public switched telephone network (PSTN), a cellular phone based network, and the like. Alternatively, the communication system 712 may be a local area network (LAN), a campus area network (CAN), a metropolitan area network (MAN), or a wide area network (WAM). The communication system 712 serves to provide a network that facilitates the transfer/receipt of information such as cardiac signal waveforms, ventricular and atrial heart rates.

The server 702 is a computer system that provides services to other computing systems over a computer network. The server 702 controls the communication of information such as cardiac signal waveforms, ventricular and atrial heart rates, and detection thresholds. The server 702 interfaces with the communication system 712 to transfer information between the programmer 706, the local RF transceiver 708, the user workstation 710 as well as a cell phone 714 and a personal data assistant (PDA) 716 to the database 704 for storage/retrieval of records of information. On the other hand, the server 702 may upload raw cardiac signals from an implanted lead 722, surface ECG unit 722 or the IMD 100 via the local RF transceiver 708 or the programmer 706.

The database 704 stores information such as cardiac signal waveforms, ventricular and atrial heart rates, detection thresholds (shown in FIG. 2), and the like, for a single or multiple patients. The information is downloaded into the database 704 via the server 702 or, alternatively, the information is uploaded to the server from the database 704. The programmer 706 is similar to the external device 600 and may reside in a patient's home, a hospital, or a physician's office.

The programmer 706 interfaces with the lead 722 and the IMD 100. The programmer 706 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 706 to the IMD 100. The programmer 706 is able to acquire cardiac signals from the surface of a person (e.g., ECGs), intra-cardiac electrogram (e.g., IEGM) signals from the IMD 100, and/or cardiac signal waveforms, ventricular and atrial heart rates, and detection thresholds from the IMD 100. The programmer 706 interfaces with the communication system 712, either via the internet or via POTS, to upload the information acquired from the surface ECG unit 720, the lead 722 or the IMD 100 to the server 702.

The local RF transceiver 708 interfaces with the communication system 712 to upload one or more of cardiac signal waveforms, ventricular and atrial heart rates, and detection thresholds (shown in FIG. 2) to the server 702. In one embodiment, the surface ECG unit 720 and the IMD 100 have a bi-directional connection 724 with the local RF transceiver 708 via a wireless connection. The local RF transceiver 708 is able to acquire cardiac signals from the surface of a person, intra-cardiac electrogram signals from the IMD 100, and/or cardiac signal waveforms, ventricular and atrial heart rates, and detection thresholds from the IMD 100. On the other hand, the local RF transceiver 708 may download stored cardiac signal waveforms, ventricular and atrial heart rates, and detection thresholds 246, and the like, from the database 704 to the surface ECG unit 720 or the IMD 100.

The user workstation 710 may interface with the communication system 712 via the internet or POTS to download cardiac signal waveforms, ventricular and atrial heart rates, and detection thresholds via the server 702 from the database 704. Alternatively, the user workstation 710 may download raw data from the surface ECG units 720, lead 722 or IMD 700 via either the programmer 706 or the local RF transceiver 708. Once the user workstation 710 has downloaded the cardiac signal waveforms, ventricular and atrial heart rates, or detection thresholds, the user workstation 710 may process the information in accordance with one or more of the operations described above. The user workstation 710 may download the information and notifications to the cell phone 714, the PDA 716, the local RF transceiver 708, the programmer 706, or to the server 702 to be stored on the database 704. For example, the user workstation 710 may communicate data to the cell phone 714 or PDA 716 via a wireless communication link 726.

Figure 8:
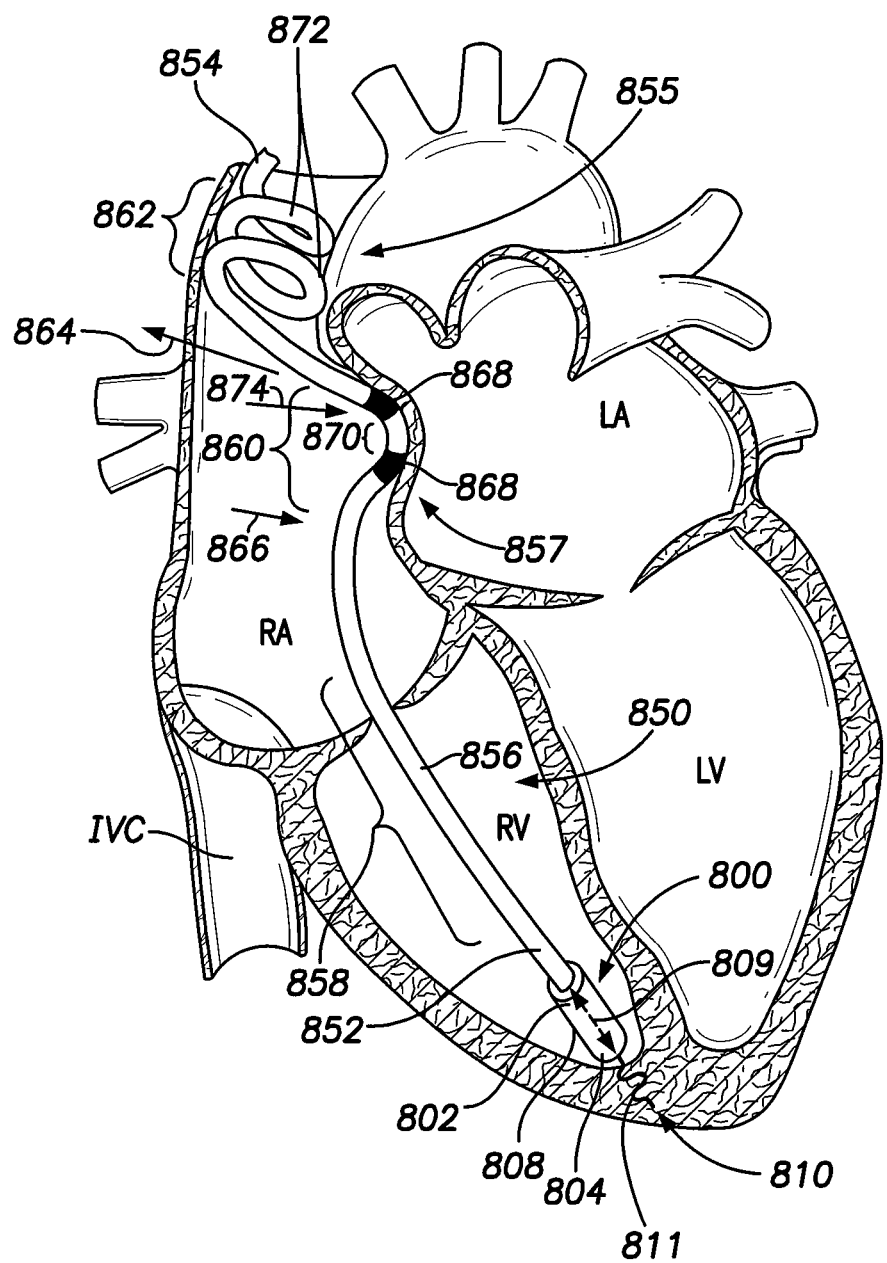
FIG. 8 illustrates an IMD formed in accordance with an alternative embodiment.

FIG. 8 provides a sectional view of the patient's heart and shows an implantable medical device (IMD) 800. The IMD 800 has been placed in the right ventricle of the heart. As another option, the IMD 800 may be introduced into the left atrium. The IMD 800 is formed in accordance with an embodiment and may represent a cardiac resynchronization device, a cardioverter, a defibrillator and the like. The IMD 800 may sense in two chambers, pace/shock in two chambers and inhibit pacing/shocking in either chamber based on intrinsic events sensed in that chamber or in the other chamber. The IMD 800 may be implanted entirely within a single local chamber of the heart. For example, the IMD 800 may be implanted entirely and solely within the right atrium or entirely and solely within the right ventricle. Optionally, the IMD 800 may be implanted entirely and solely within the left atrium or left ventricle through more invasive implant methods.

The IMD 800 includes a housing 802 that includes a base 804 and a top end 811. The housing 802 extends along a longitudinal axis 809 between the base 804 and the top end 811. The housing 802 is elongated and tubular in shape and extends along the longitudinal axis 809. The base 804 is configured to be secured to the local chamber. In the example of FIG. 1, the base 804 is secured to the right ventricle. Optionally, the IMD 800 may be located in, and the base 804 secured to the wall of the left ventricle, left atrium or right atrium.

The base 804 includes an active fixation member 810 provided thereon and extending outward from the base 804 in a direction generally along the longitudinal axis 809. A first electrode 811 (also referred to as an active electrode area) is provided on the active fixation member 810. The electrode 811 is provided at a first position such that, when the IMD is implanted in the local chamber, the first electrode 811 engages the local wall tissue at a local activation site within the conduction network of the local chamber (e.g., within the ventricular wall tissue at the apex of the right ventricle).

An intra-cardiac (IC) device extension 850 has a proximal end 852, a distal end 854 and a extension body 856 extending there between. The term "intra-cardiac" is used to indicate that the device extension 850 "generally" remains within the heart and associated vessels, such as the SVC, IVC, CS, pulmonary arteries and the like. The term "device" is used to indicate that the extension 850 is an extension of the IMD 800. The proximal end 852 is permanently or removably (through a header style connector) coupled to the housing 802 and located in the local chamber. A stabilization arm, generally denoted at 855, is provided on the distal end 852 of the extension body 856. A right atrial appendage (RAA) fixation mechanism, generally denoted at 857, is provided at an intermediate point along the length of the extension body 856 and aligned with the RAA.

In the example of FIG. 8, the extension body 856 including a chamber transition sub-segment 858, an active interim-segment 860 and a stabilizer end-segment 862. The stabilization end-segment 862 is one exemplary structural implementation of the stabilization arm. The RAA fixation mechanism 857 is one exemplary structural implementation of an active interim-segment 860. The chamber transition sub-segment 858 is sufficient in length to extend from the local chamber (e.g., the right ventricle) through the tricuspid valve into an adjacent chamber (e.g., the right atrium). The chamber transition sub-segment 858 extends upward out of the right ventricle in a direction that generally follows the longitudinal axis 809.

The extension body 856 is formed of a biocompatible insulated material such as EFTE, silicon, OPTIM and the like. The stabilizer end-segment 862 is located at the distal end 854 and in a pre-formed shape that is biased to extend slightly outward in a lateral direction (generally denoted at 864) relative to a length of the chamber in which the stabilizer end-segment 862 is located. The stabilizer end-segment 862 engages a first region of the heart. For example, the stabilizer end-segment 862 may extend upward into and engage the SVC. Optionally, the stabilizer end-segment 862 may extend downward into and engage the IVC. The stabilizer end-segment 862 is pre-formed into a predetermined shape based upon which portion of the chamber is to be engaged. The stabilizer end-segment 862 may be formed with turns 872 that radially expand to a different diameter sufficient to firmly fit against the interior walls of the IVC. Optionally, the stabilizer end-segment 862 may utilize alternative shapes for SVC stabilization, such as an S-shape, a T-shape, a Y-shape, a U-shape and the like. Optionally, the stabilizer end-segment 862 may be split into multiple (e.g., 2-4) stabilizer end-segments that project outward in different directions and contact different areas of the wall tissue.

The active interim-segment 860 is biased, by the stabilizer end-segment 862, to extend in a second transverse direction 866 away from the direction 864 and toward the septum or atrial appendage. The active interim-segment 860 has a pre-formed curved shape, such as a large C-shape, or U-shape. The active interim-segment 860 includes one or more electrodes 868 that are provided thereon and in a trough area 874 of the C-shape or U-shape. The electrodes 868 are spaced apart from one another, within the trough area 874, by an inter-electrode spacing 870. The trough area 874 of the active interim-segment 860, and thus the electrodes 868, are biased in the transverse appendage or septal direction 8 11 11 to engage a second region of wall tissue of the adjacent chamber in which the active interim-segment 860 is located. For example, the second electrodes 868 may be biased to engage wall tissue in the right atrial appendage. The second electrodes 868 engage distal wall tissue at a distal activation site (relative to the chamber which the IMD 800 is implanted) within the conduction network of the adjacent chamber.

Figure 9:
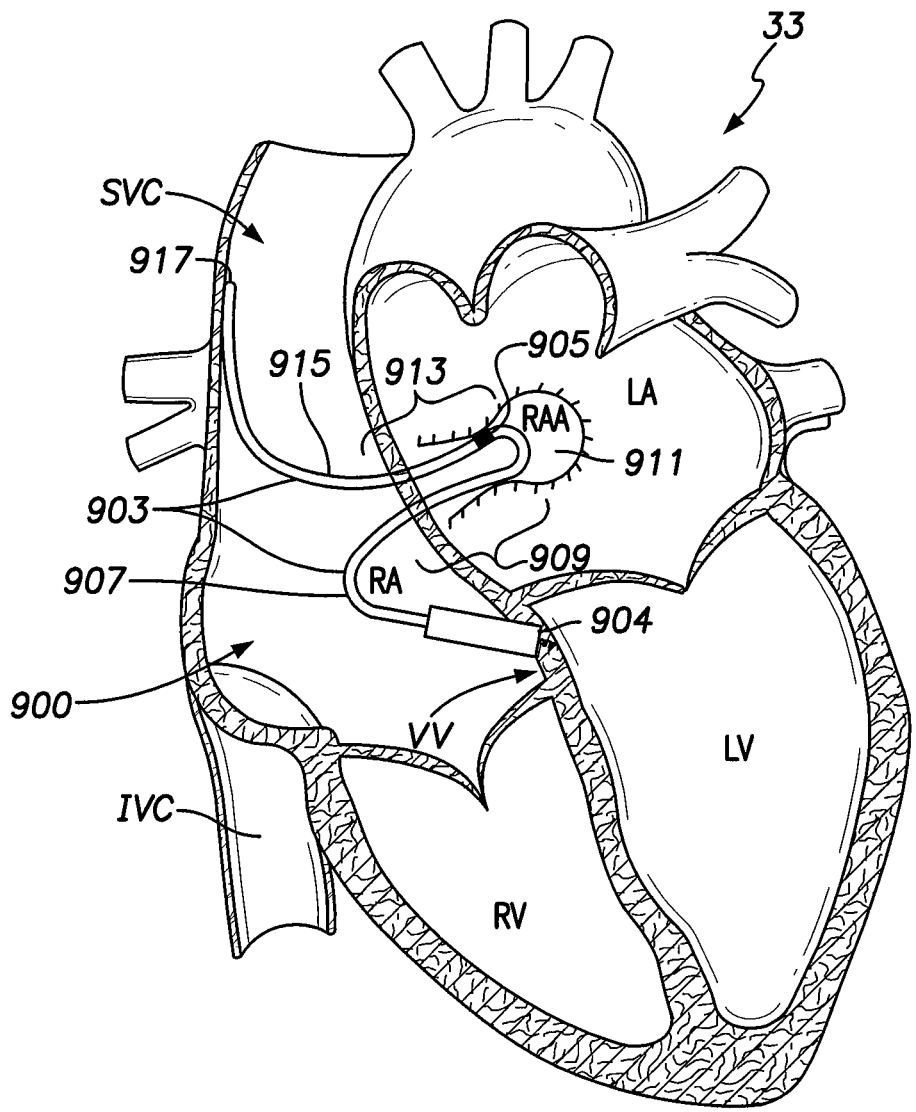
FIG. 9 illustrates an IMD formed in accordance with an alternative embodiment.

FIG. 9 provides a sectional view of the patient's heart and shows an IMD 900. The IMD 900 comprises a housing configured to be implanted entirely within a single local chamber of the heart. The housing includes a proximal base end and a distal top end. The proximal base end includes an active fixation member, such as a helix, that is illustrated to be implanted in the ventricular vestibule (VV). A shaped IC device extension 903 extends from the distal top end of the housing. The IC device extension 903 comprises an elongated body that may be tubular in shape and may include a metal braid provided along at least a portion of the length therein (as explained herein in more detail). The extension body including a transition sub-segment, an active interim-segment and a stabilizer end-segment, all of which are illustrated in a deployed configuration and some of which are preloaded against anatomical portions of tissue of interest. For example, the active interim-segment (e.g., second curved segment 911, and all or portions of the first and second linear regions 909 and 913) and the stabilizer end-segment (e.g., third curved segment 915 and all or portions of the second linear region 913) are shown preloaded against anatomical tissue of interest. The braid resists torque compression but permits lateral flex. One or more electrodes 905 are carried by the IC device extension 903 and are electrically connected to electronics within the housing through conductors extending through the body of the IC device extension.

The IC device extension 903 is formed with shape memory characteristics that allow the IC device extension 903 to transform between a collapsed state, in which the IC device extension assumes a substantially linear shape, and an expanded state, in which the IC device extension assumes a multiple curved shape.

The IC device extension includes a short stem that extends a short distance from the distal top end of the housing. The stem merges into a first curved segment 907 that turns at a sharp angle with respect to a longitudinal axis of the housing. Optionally, the first curved segment 907 may form an acute angle, 90 degree angle, or obtuse angle approximately with respect to a longitudinal axis of the housing. The first curved segment 907 merges into and is followed by a first generally linear region 909 that extends laterally from the housing, along a lateral axis, until merging with a second curved segment 911. The second curved segment 911 turns at a sharp angle with respect to the longitudinal axis of the housing and the lateral axis of the first linear region 909. Optionally, the second curved segment 911 may form an acute angle, 90 degree angle, or obtuse angle approximately with respect to the lateral axis of the first linear region 909. As one example, the second curved segment 911 may approximate a 180 degree sharp or "hairpin" curve away from the lateral axis of the first linear region 909 and away from the longitudinal axis of the housing. The second curved segment 911 merges into and is followed by a second generally linear region 913 that extends along a second lateral direction.

One or more electrodes 905 are located along the second curved segment 911. Optionally, the electrode(s) may be provided in the region proximate to the junction of the second curved segment 911 and the second linear region 913. Optionally, one or more electrodes 905 may be provided along the second linear region 913.

The second linear region 913 merges with and extends to a third curved segment 915. The third curved segment 915 follows an extending "slow" arc and then terminates at a tail end 917 of the IC device extension 903. The third curved segment 915 follows a slow arc with respect to the longitudinal axis of the housing and the lateral axis of the first linear region 909. As one example, the third curved segment 915 may approximate a 90 degree turn away from the longitudinal axis of the housing until terminating at the tail end 917 of the IC device extension.

FIG. 10 illustrates an IMD 1000 formed in accordance with an alternative embodiment. The IMD 1000 includes a body or housing 1002. The housing 1002 has a proximal base 1004 and a distal top end 1006, with the intermediate shell 1008 extending there between. The shell 1008 is elongated and may be tubular in shape to extend along a longitudinal axis 1009. The base 1004 includes at least one electrode 1012. The electrode 1012 may be a helical shaped screw to actively secure the base 1004 at a desired site within a selected local chamber of the heart. The electrode 1012 includes a conductor that is surrounded by insulation along the majority of the length thereof, but exposes the distal tip 1014 of the conductor.

The IMD 1000 further includes an appendage arm 1020 pivotally connected to and extending outward from the top end 1006. The appendage arm 1020 includes a distal end 1022 upon which an electrode 1024 is located. The appendage arm 1020 includes a proximal end 1026 that is rotatably coupled through a hinge assembly 1042 to the top end 1006 of the housing 1002. The appendage arm 1020 extends along an appendage axis 1028 and rotates along the appendage rotation arc 1044 between limits. The hinge assembly 1042 is configured to permit the appendage arm 1020 to rotate from a collapsed installation position to a deployed implanted position. When in the collapsed position, the appendage arm 1020 is rotated in the direction of arrow 1043 until the appendage axis 1028 forms a very small acute angle, or is oriented substantially parallel to, a longitudinal axis 1009 of the shell 1008 of the IMD 1000. When in the deployed position, the appendage arm 1020 rotates in the direction of arrow 1046 until reaching a fully deployed outer limit of the arc of rotation as defined by the hinge assembly 1042. When fully deployed, the appendage axis 1028 projects outward at a larger acute angle (e.g. 10-1 100°) from the longitudinal axis 1009 of the shell 1008. The outer limit of the deployed position for the appendage arm 1020 is controlled by the rotation range permitted at the hinge assembly 1042 and may have spring tension tensioning it with respect to the stabilizer arm or the housing 1002.

The IMD 1000 also includes a stabilizer arm 1030 having a distal end 1032 and a proximal end 1036. The distal end 1032 is formed integral with a pusher cup 1034 that includes some type of pusher reception feature, such as a pusher receptacle 1040. The pusher cup and receptacle 1034 and 1040 are configured to receive an external pusher tool that is used by the physician when implanting the IMD 1000 (as explained below in more detail). As one example, the pusher receptacle 1040 may include a threaded recess 1041 that is configured to threadably and securely receive a tip of the pusher tool to ensure a secure attachment to the pusher tool during installation. Once the IMD 1000 is fully implanted, the tip of the pusher tool is unscrewed from the threaded receptacle 1041. An expandable collet may be used, instead of a screw to attach the pusher tool to the stabilizer arm 1030.

The stabilizer arm 1030 is rotatably secured, at its proximal end 1036, to the hinge assembly 1042 to permit the stabilizer arm 1030 to rotate along arc 1046. The stabilizer arm 1030 may be rotated between a collapsed installation position at which the stabilizer axis 1038 is arranged at a very small acute angle or substantially parallel to the longitudinal axis 1009. Once implanted, the stabilizer arm 1030 is then permitted to rotate outward along arc 1046 to a deployed position such that the stabilizer axis 1038 forms a larger acute angle (e.g. 10-1 100°) with respect to the longitudinal axis 1009. The hinge assembly 1042 controls the range of rotation afforded to the stabilizer arm 1030 and may have spring tension tensioning it with respect to the appendage arm 1020 or the housing 1002. At least one of the stabilizer arm 1030 and appendage arm 1020 may be constructed to have a core structure that is torque and compression resistant such that when the pusher tool is rotated or moved longitudinally, the stabilizer arm 1030 and/or appendage arm 1020 conveys rotational and longitudinal force from the pusher tool to the housing of the IMD 1000. For example, the core structure may include a metal (e.g. aluminum or stainless steel) braid encased in a biocompatible material, such as PTFE, ETFE or silicon rubber. The braid may have a hollow core in which insulated conductors run between electrodes and the IMD 1000.

Optionally, the stabilizer arm 1030 may be fixedly secured to the distal end 1006 of the IMD 1000, such that the stabilizer arm 1030 does not rotate relative to the longitudinal axis 1009. Instead, in this alternative embodiment, the stabilizer arm 1030 is rigidly secured to the distal end 1006 and may be oriented such that the stabilizer axis 1030 extends directly parallel or at an angle to the longitudinal axis 1009 at all times, during installation and after deployment. Again, the stabilizer arm 1030 and the appendage arm 1020 collectively form an IC device extension.

As a further option, a pusher cup or multiple pusher cups 1050 may be provided about the exterior surface of the shell 1008 or on the distal top end 1006. The pusher cup 1050 includes a pusher receptacle 1052 configured to receive the tip of a pusher tool that is used during implantation.

FIG. 11 illustrates an IMD 1100 that resembles the IMD 1000, except that the appendage arm 1120 and stabilizer arm 1130 are configured in a manner different than those of FIG. 10. In the embodiment of FIG. 11, the stabilizer arm 1130 and appendage arm 1120 are integrally joined with one another in a base area 1121, but are formed of a flexible material that has a desired preformed resting shape, corresponding to the deployed configuration illustrated in FIG. 11. When in the deployed position, the stabilizer arms 1128 and 1130 are flared outward away from one another by an angle denoted at 1144.

The appendage arm 1120 and stabilizer arm 1130 have a common proximal end 1136 that is secured to the top end 1106 of the body 1102. The appendage arm 1120 has a distal end 1122 with an electrode 1124 thereon as configured to passively or actively engage tissue at a desired activation site.

The stabilizer arm 1130 has a distal end 1132 at which a pusher cup 1134 is formed integral therewith. The pusher cup 1134 includes a pusher receptacle 1140 that is configured to receive a pusher tool during installation. During installation, the appendage arm 1120 and stabilizer arm 1130 are flexed inward to collapse against one another such that the angle 1144 is very small or approximately zero in order that the appendage axis 1128 and stabilizer axis 1138 extend substantially parallel to the longitudinal axis 1109 of the IMD 1100. When the appendage and stabilizer arms 1120 and 1130 are collapsed against one another, the outer envelope thereof is no greater than the outer envelope of the shell 1108 to provide a form factor small enough to be received within an introducer for installation in a desired chamber of the heart.

The IMD 1100 includes a body or housing 1102 having a shell 1108 that hermetically encloses the electronics, controller, battery, charge storage unit, and all other electrical components of the IMD 1100. The housing 1102 has a proximal base 1104 and a distal top end 1106, with the intermediate shell 1108 extending there between. The shell 1108 is elongated and may be tubular in shape to extend along a longitudinal axis 1109. The base 1104 includes at least one electrode 1112. The electrode 1112 may be a helical shaped screw to actively secure the base 1104 at a desired site within a selected local chamber of the heart.

The IMD 1100 further includes an appendage arm 1120 pivotally connected to and extending outward from the top end 1106. The appendage arm 1120 includes a distal end 1122 upon which an electrode 1124 is located. The electrode 1124 may be a passive electrode that is configured to simply rest against a select activation site. The IMD 1100 also includes a stabilizer arm 1130 having a distal end 1132 and a proximal end 1136. The distal end 1132 is formed integral with a pusher cup 1134 that includes some type of pusher reception feature, such as a pusher receptacle 1140. The stabilizer arm 1130 may be flexed between a collapsed installation position at which the stabilizer axis 1138 is arranged at a very small acute angle or substantially parallel to the longitudinal axis 1109. Once implanted, the stabilizer arm 1130 is then permitted to return to its flared state to a deployed position such that the stabilizer axis 1138 forms a larger acute angle with respect to the longitudinal axis 1109.

Optionally, the stabilizer arm 1130 may be fixedly secured to the distal end 1106 of the IMD 1100, such that the stabilizer arm 1130 does not rotate relative to the longitudinal axis 1109. Instead, in this alternative embodiment, the stabilizer arm 1130 is rigidly secured to the distal end 1106 and may be oriented such that the stabilizer axis 1130 extends directly parallel to the longitudinal axis 1109 at all times, during installation and after deployment. Again, the stabilizer arm 1130 and the appendage arm 1120 collectively form an IC device extension.

Optionally, embodiments may be implemented in which electrodes are not located in each chamber for which beats or cardiac events are sensed. Instead, electrode configurations may be utilized such that the electrodes are only located in are one chamber of the heart or a chamber(s) adjacent to the chamber for which it is determined where beats originate. For example, an IMD may be used that is configured to be implanted entirely within a single local chamber of the heart and remote from an adjacent chamber. However, the IMD may determine whether beats originate in the local chamber or an adjacent chamber, even though no electrodes are physically located in the adjacent chamber. It is understood that the IMD may be implanted within any chamber of the heart which then would constitute the "local" chamber, while the other three chambers of the heart would constitute "adjacent" chambers. Hence, if the IMD is implanted in the left ventricle, then the LV is the local chamber, while the RV, RA and LA would represent adjacent chambers. Similarly, if the IMD is implanted in the left atrium, then the LA is the local chamber, while the RV, RA and LV represent adjacent chambers.

The electrodes may be configured to perform near field (NF) and far field (FF) sensing over NF and FF channels. The IMD collects NF and FF signals at the same time and end at the same or different times. The NF and FF channels may be configured to function as atrial and ventricular sensing channels, as a pair of atrial channels, as a pair of ventricular channels and the like. The FF sensing circuit in the IMD senses electrical signals over a far field (FF) channel, such as an atrial channel, for the duration of the FF sensing window. Optionally, if the IMD is implanted in the left ventricle, then the FF channel may represent an RV channel, RA channel and/or LA channel as the RV, RA and LA represent adjacent chambers. Similarly, if the IMD is implanted in the left atrium, then the FF channel may represent the RV, RA and/or LV channel, as the RV, RA and LV represent adjacent chambers. The FF signals sensed over the FF channel include signals representative of activity originating in one or more adjacent chambers. The FF signals may be representative of cardiac events or cardiac activity that occurs intrinsically or that corresponds to a paced event.

The FF signals are sensed over the FF channel by a first electrode combination that is provided on or near the local chamber. The NF signals are sensed over the NF channel by a second electrode combination that is provided on or near the local chamber. The first and second electrical combinations may at least partially overlap (e.g., use a common electrode). For example, the first electrode combination may include an electrode pair such as the distal and intermediate electrodes. The second electrode combination may include another electrode pair such as the proximal and intermediate electrodes. Optionally, one or both of the first and second electrode combinations may include other single electrodes, pairs of electrodes, or sets of more than two electrodes.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for discriminating heart arrhythmias, the method comprising:
   identifying an arrhythmia;

recording a predetermined number of beats over a sensing channel, during the arrhythmia, as base arrhythmia (BA) beats;

delivering anti-tachy pacing (ATP) therapy to at least one chamber of the heart;

after delivering the ATP therapy, recording at least one return beat representing cardiac activity following the ATP therapy over the sensing channel;

determining whether the return beat originated in a reference chamber of the heart;

comparing a morphology of the return beat to a morphology of the BA beat; and declaring a VT or SVT based on the comparing operation.

2. The method of claim 1, wherein the declaring operation includes declaring a VT when the morphology of the return beat corresponds to the morphology of the BA beat and the sensing channel is an RV sensing channel.

3. The method of claim 1, further comprising determining whether the arrhythmia persists following delivery of the ATP therapy.

4. The method of claim 1, wherein the determining operation includes determining whether the return beat originates in a ventricle as the reference chamber.

5. The method of claim 1, wherein the determining operation includes determining whether the return beat originates in an RA or RV as the reference chamber.

6. The method of claim 1, wherein the BA morphology is derived from a series of at least 3 beats as the predetermined number of beats.

7. The method of claim 1, wherein the delivering operation includes delivering the ATP therapy to both of the RV and RA.

8. The method of claim 1, wherein the comparing operation includes comparing a QRS complex of the return beat and the BA beat.

9. The method of claim 1, wherein the return beat represents a first intrinsic cardiac event that occurs immediately after completion of the ATP therapy.

10. The method of claim 1, wherein the sensing channel is an RA sensing channel and the comparing operation includes comparing the return beat sensed over the RA sensing channel to the BA morphology sensed over the RA sensing channel when the return beat originates in the RA.

11. The method of claim 1, wherein the comparing operation includes at least one of the following:
   i) comparing shapes of the BA and return beats,
   ii) comparing a number of peaks in the BA and return beats,
   iii) comparing an area under curves defined by the BA and return beats,
   iv) comparing a number of polarity changes in the BA and return beats, and
   v) comparing a number of positive and negative peaks in the BA and return beats.

12. A system for discriminating heart arrhythmias, the system comprising:

inputs configured to receive cardiac signals representative of heart beats over a sensing channel;

an arrhythmia module configured to identify an arrhythmia;

a processor configured to record in memory the cardiac signals for a predetermined number of beats, during the arrhythmia, as a base arrhythmia (BA) beats;

a therapy module configured to deliver anti-tachy pacing (ATP) therapy to at least one chamber of the heart;

the processor, configured to record in the memory, after delivering the ATP therapy, the cardiac signals for at least one return beat representing cardiac activity following the ATP therapy as sensed over the sensing channel;

an origin module configured to determine whether the return beat originated in a reference chamber of the heart;

a morphology module configured to compare a morphology of the return beat to a morphology of the BA beat; and a declaration module configured to declare a VT or SVT based on the comparing operation.

13. The system of claim 12, wherein sensing channel is an RV sensing channel and the declaration module is configured to declare a VT when the morphology of the return beat corresponds to the morphology of the BA beat.

14. The system of claim 12, wherein the arrhythmia module is configured to determine whether the arrhythmia persists following delivery of the ATP therapy.

15. The system of claim 12, wherein the origin module is configured to determine whether the return beat originates in a ventricle as the reference chamber.

16. The system of claim 12, wherein the origin module is configured to determine whether the return beat originates in an RA or RV as the reference chamber.

17. The system of claim 12, wherein the morphology module is configured to derive the morphology of the BA beat from a series of at least 3 beats as the predetermined number of beats.

18. The system of claim 12, wherein the therapy module is configured to deliver the ATP therapy to both of the RV and RA.

19. The system of claim 12, wherein the morphology module is configured to compare a QRS complex of the return beat and the BA beat.

20. The system of claim 12, wherein the morphology module is configured to compare at least one of the following:
   i) shapes of the BA and return beats,
   ii) a number of peaks in the BA and return beats,
   iii) an area under curves defined by the BA and return beats,
   iv) a number of polarity changes in the BA and return beats, and
   v) a number of positive and negative peaks in the BA and return beats.

* * * * *